United States Patent
Freedman

(10) Patent No.: US 6,229,308 B1
(45) Date of Patent: May 8, 2001

(54) FORMATION EVALUATION USING MAGNETIC RESONANCE LOGGING MEASUREMENTS

(75) Inventor: Robert Freedman, Houston, TX (US)

(73) Assignee: Schlumberger Technology Corporation, Houston, TX (US)

( * ) Notice: Subject to any disclaimer, the term of this patent is extended or adjusted under 35 U.S.C. 154(b) by 0 days.

(21) Appl. No.: 09/429,802

(22) Filed: Oct. 29, 1999

Related U.S. Application Data

(60) Provisional application No. 60/109,252, filed on Nov. 19, 1998.

(51) Int. Cl.$^7$ ...................................................... G01V 3/00
(52) U.S. Cl. ......................... 324/303; 324/300; 324/307; 324/312
(58) Field of Search .................................. 324/303, 300, 324/307, 312

(56) References Cited

U.S. PATENT DOCUMENTS

| | | | |
|---|---|---|---|
| 3,597,681 | 8/1971 | Huckabay et al. | 324/5 R |
| 4,710,713 | 12/1987 | Strikman | 324/303 |

(List continued on next page.)

FOREIGN PATENT DOCUMENTS

| | | |
|---|---|---|
| WO 96/29617 | 9/1996 | (WO). |
| WO 97/34166 | 9/1997 | (WO). |

OTHER PUBLICATIONS

A. Abragam, *The Principles of Nuclear Magnetism*, Oxford University Press, pp. 324–325 (1961).

R. Akkurt, D.Mardon, J.S. Gardner, D.M. Marschall & F. Solanet, *SPWLA*, "Enhanced Diffusion: Expanding the Range of NMR Direct Hydrocarbon–Typing Methods," Paper GG, 39$^{th}$ Annual Logging Symposium (1998).

R. Akkurt, H.J. Vinegar, P.N. Tutunjian & A.J. Guillory, *SPWLA*, "NMR Logging of Natural Gas Reservoirs," Paper N, 36$^{th}$ Annual Logging Symposium (1995).

N. Bloembergen, E.M. Purcell & R.V. Pound, "Relaxation Effects in Nuclear Magnetic Resonance Absorption," *Physical Review*, vol. 73, No. 7, pp. 679–712 (1948).

(List continued on next page.)

*Primary Examiner*—Christine Oda
*Assistant Examiner*—Brij B. Shrivastav
(74) *Attorney, Agent, or Firm*—John J. Ryberg; Brigitte L. Jeffery

(57) ABSTRACT

A form of the invention is directed to a method for determining properties of earth formations surrounding a borehole, including the following steps: (a) providing a logging device that is moveable through the borehole; (b) transmitting electromagnetic energy from the logging device into the formations, and receiving nuclear magnetic resonance spin echoes at the logging device; (c) performing step (b) a plurality of times, with a respective plurality of different transmitting and/or receiving conditions to obtain a plurality of measurements; (d) generating a formation model that includes a plurality of model components for a brine phase and a plurality of model components for a native oil phase; (e) modifying the model components to optimize the model with respect to the measurement signals; and (f) outputting model components of the optimized model. Depending on the circumstances, the step (d) of generating a formation model can include generating a model that further includes an oil base mud filtrate component and/or can include a gas component. In an embodiment of the invention, the step (d) of generating a formation model includes generating a set of model amplitude components that define the transverse relaxation time distribution of the brine phase, and a further set of model amplitude components that define the transverse relaxation time distribution of the native oil, and a further set of model components that define the constituent viscosities of the native oil.

82 Claims, 15 Drawing Sheets

U.S. PATENT DOCUMENTS

| | | | |
|---|---|---|---|
| 5,041,975 | 8/1991 | Minerbo et al. | 324/303 |
| 5,055,788 | 10/1991 | Kleinberg et al. | 324/303 |
| 5,291,137 | 3/1994 | Freedman | 324/303 |
| 5,663,499 | 9/1997 | Semmelbeck et al. | 324/303 |
| 6,069,477 * | 5/2000 | Chen et al. | 324/303 |
| 6,109,368 * | 8/2000 | Goldman et al. | 175/39 |

OTHER PUBLICATIONS

A. Bondi, *Physical Properties of Molecular Crystals, Liquids and Glasses*, John Wiley & Sons, pp. 337–369 (1968).

S. Chen, O. Olima, H. Gamin, D. Georgi & J. Minetto, SPE, "Estimation of Hydrocarbon Viscosity with Multiple TE Dual Wait–Time MRIL Logs," Annual Technical Conference Paper 49009, pp. 213–226 (1998).

R. Freedman & G. Rouault, *SPE Formation Evaluation*, "Remaining–Oil Determination using Nuclear Magnetism Logging," pp. 121–130 (Jun. 1989).

R. Kleinberg & H.J. Vinegar, *Log Analyst*, "NMR Properties of Reservoir Fluids," pp. 20–32 (Nov.–Dec. 1996).

S. Lo, G. Hirasaki, R. Kobayashi & W. House, *Log Analyst*, "Relaxation Time and Diffusion Measurements of Methane and n–Decane Mixtures," pp. 43–46 (Nov.–Dec. 1998).

W. Looyestijn, *SPWLA*, "Determination of Oil Saturation for Diffusion NMR Logs," Paper SS, 37$^{th}$ SPWLA Meeting (1996).

W. McCain, *The Properties of Petroleum Fluids*, Ch. 1, pp. 1–45, PennWell Publishing Co. 2$^{nd}$ Ed. (1990).

C. Morriss, R. Freedman, C. Straley, M. Johnston, H. Vinegar & P. Tutunjian, *SPWLA*, "Hydrocarbon Saturation and Viscosity Estimation from NMR Logging in the Belridge Diatomite," Paper C, 35$^{th}$ Meeting SPWLA (1994).

A. Peressini, F. Sullivan & J. Uhl Jr., *The Mathematics of Nonlinear Programming*, Ch. 5 pp. 157–212, Springer Verlag Pub. Co. (1988).

K. Schittkowski, "NLPQL: A Fortran Subroutine Solving Constrained Nonlinear Programming Problems," *Annals of Operations Research*, v. 5, pp. 485–500(1985).

A. Stuart & K. Ord, *Kendall's Advanced Theory of Statistics vol. 2*, 5$^{th}$ ed., Oxford Univ. Press, pp. 649–706 (1991).

Q. Zhang, S. Lo, C. Huang, G. Hirasaki, R. Kobayashi & W. House, *SPWLA*, "Some Exceptions to Default NMR Rock and Fluid Properties," Paper FF, 39$^{th}$ Annual SPWLA Meeting (1998).

M.D. Hurlimann, *J. Magnetic Resonance 131*, "Effective Gradients in Porous Media due to Susceptibility Differences," Article No. MN981364, pp. 232–24–(1998).

D. Forster, *Hydrodynamic Fluctuations, Broken Symmetry, and Correlation Functions*, Chap. 6, pp. 121–137, W. A. Benjamin, Inc. Publishers (Reading, Mass. 1975).

M.J.D. Powell, "Tolmin: A Fortran Package for Linearly Constrained Optimization Calculations," Numerical Analysis Report DAMTP 1989/NA2, Univ. of Cambridge, Cambridge, England (Mar. 1989).

\* cited by examiner (METHANE)

(PROPANE)

(PROPENE)

(CYCLOHEXANE)

(1.3 CYCLOHEXADIENE)

+ - - - - - - - - - -

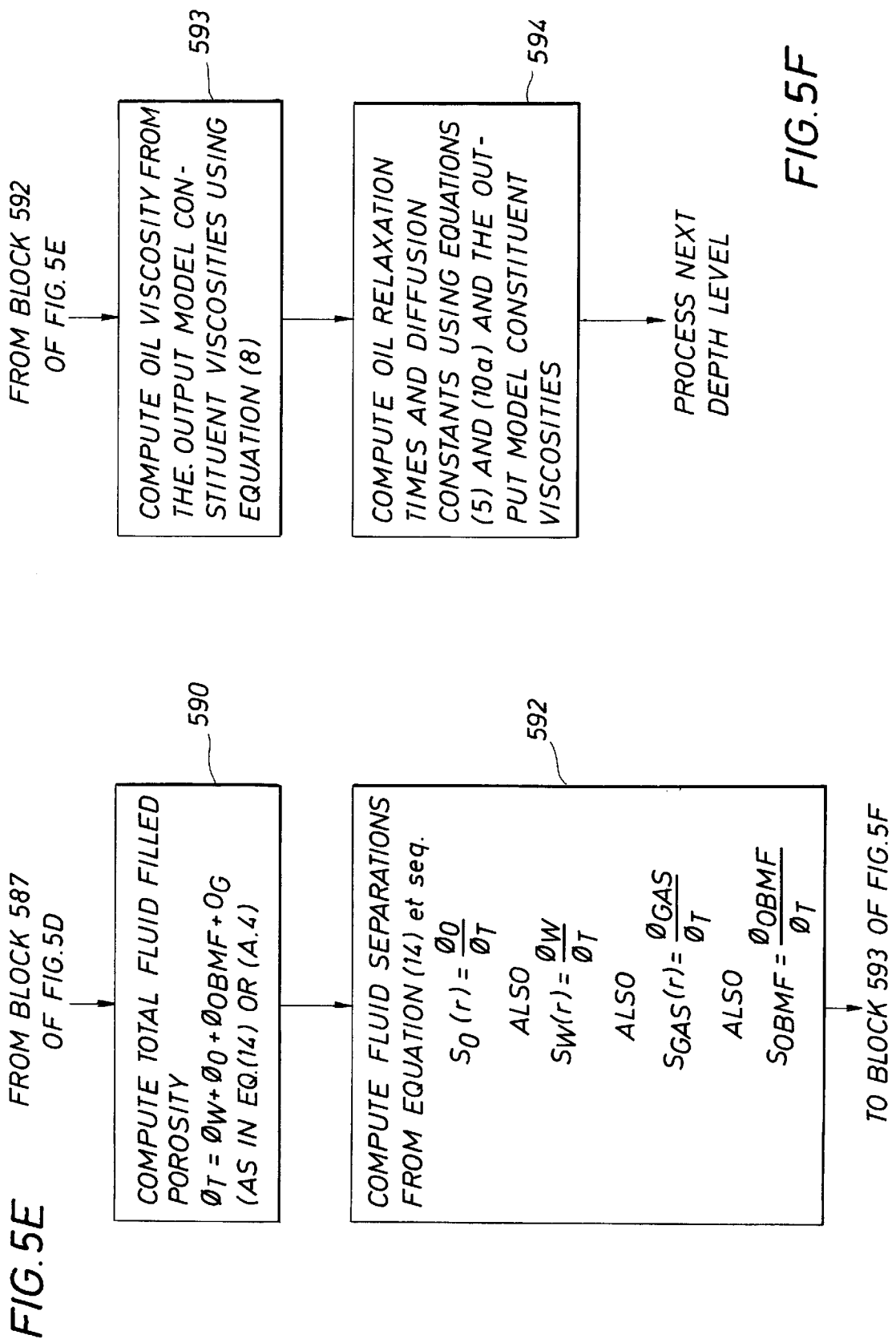

FORMATION EVALUATION USING MAGNETIC RESONANCE LOGGING MEASUREMENTS

RELATED APPLICATION

This application claims priority from U.S. Provisional Patent Application Ser. No. 60/109,252, filed Nov. 19, 1998, and said U.S. Provisional Patent Application is incorporated herein by reference.

FIELD OF THE INVENTION

This invention relates to nuclear magnetic resonance techniques and, more particularly, to a method for evaluating a formation using nuclear magnetic resonance measurements.

BACKGROUND OF THE INVENTION

Conventional formation evaluation methods for detecting hydrocarbons have relied largely on electrical log measurements of either formation resistivity or conductivity and on measurements of formation porosity from neutron, density or sonic tool measurements. The utility of electrical log measurements for hydrocarbon detection, and also for quantitative estimation of hydrocarbon saturations, is dependent on empirically based saturation equations like the well known Archie equation or others including the Waxman-Smits and Dual-Water models. In many environments this traditional approach to formation evaluation provides accurate reservoir predictions. Nonetheless, the following types of occurrences are not uncommon: missed pay zones, inaccurate estimates of hydrocarbons in place and costly completions of zones that are not commercial. The causes of these occurrences include formation waters of unknown or variable salinity, fresh formation waters, clay conductance effects on measured resistivity, inaccurate inversion of resistivity data, and formations that have anomalous values for the Archie parameters.

The evaluation of hydrocarbon reservoirs using pulsed NMR logging tools offers the potential to provide a solution to the problem in formnation evaluation stemming from the fact that many hydrocarbon reservoirs can be misinterpreted or even missed altogether by conventional resistivity based evaluation methods.

An NMR approach that uses a "differential methodology" was proposed in publications of Akkurt, et al. (NMR Logging Of Natural Gas Reservoirs, Paper N presented at the 36$^{th}$ Annual Meeting of the Society of Professional Well Log Analysts, 1995). This methodology involves making two NMR spin-echo measurements with different wait times; that is, different times for polarization or re-polarization of the spins. The raw measurements (detected spin echo signals), or the $T_2$-distributions computed from these measurements, are subtracted to yield a "differential signal" (either a differential $T_2$ spectrum or echo train) that can be further processed to estimate hydrocarbon filled porosity. In the NMR well logging literature, some of the differential methods are called differential spectrum method (DSM) and time domain analysis (TDA). The wait times of the methods are selected so that the differential signal contains small contributions from the brine in the formation. In order to select proper wait times so that the brine contribution is canceled, knowledge of the NMR properties of the fluids in the formation is required. This is a limitation of these methods for oil exploration logging. Moreover, the interpretation of the technique requires that the T, distribution of the brine phase not overlap with the $T_1$ spectra of the hydrocarbon phases. In carbonate reservoirs and in reservoirs containing light to intermediate viscosity oils (e.g., 1–50 cp), the brine and hydrocarbon Tl-distributions can overlap. This limits the applicability of the differential methods to shaly sands containing very low viscosity oils and gas. A recent paper, Akkurt et al. (Enhanced Diffusion: Expanding the Range of NMR Direct Hydrocarbon-Typing Methods, Paper GG presented at the 39$^{th}$ Annual Meeting of the Society of Professional Well Log Analysts, 1998) noted the limitations of the DSM and TDA methods for oils with intermediate viscosities and proposed a method called the Enhanced Diffusion Method (EDM) that attempts to exploit the fact that the brine phase is more diffusive than intermediate viscosity oils. By increasing the echo spacing so that diffusion dominates the $T_2$ relaxation of the brine, an upper limit ($T_{2DW}$) on the apparent $T_2$ can be achieved. To obtain the oil filled porosity, the Akkurt, et al. 1998 paper proposed integrating the apparent $T_2$-distribution for relaxation times greater than $T_{2WD}$. Although the basic concept of the EDM is believed to be valid, there are complications in practice that limit its reliability for detection of oil, including: (1) the apparent $T_2$-distributions are broadened by the regularization (smoothing) that is applied by the processing to reduce noise artifacts, so integrating the apparent $T_2$-distributions from a sharp brine cutoff can lead to predictions of oil in water zones; (2) the oil signal can have a short relaxation time tail that extends into the brine signal; (3) in exploration wells it cannot be assumed that the diffusivity of formation oils is less than that of water; and (4) in wells drilled with oilbase muds, it is difficult using the EDM concept to separate the filtrate signal from that of the native oil.

A recent paper by Chen et al. (Estimation of Hydrocarbon Viscosity With Multiple TE Dual Wait-Time MRIL Logs, Paper 49009 in the Transactions of the 1998 SPE Annual Technical Conference and Exhibition, 1998), proposes a method for combining dual-wait time and multiple echo spacing data to estimate oil viscosity. The differential methodology is used to combine the different measurements. The spin-echo trains from long and short wait time data acquired with the same echo spacing are subtracted to eliminate the water brine signal. This method has the limitations discussed above. Furthermore, the subtraction of the differential signal increases the noise by a factor of 1.4 which is also one of the drawbacks of the TDA method.

A fundamental weakness of the aforementioned inversion methods is that separation of the measured data into brine and hydrocarbon signals is only done in an ad hoc manner in fitting the differential signal. An approach that makes this separation at the outset is disclosed in Looyestijn (Determination of Oil Saturation from Diffusion NMR Logs, Paper SS presented at the 37th Annual Meeting of the Society of Professional Well Log Analysts, 1996), which uses "diffusion processing" to compute the oil saturation from NMR data acquired with different echo spacings. Looyestijn fits the measured data to a model that explicitly includes the brine and oil signals. The model used five simple exponentials for the brine phase and a stretched exponential for the oil phase and was applied to NMR log data from a development well drilled with a waterbase mud. The oil relaxation times were known from lab measurements on produced samples and the oil and brine filled porosities were computed from the log data. In a Published PCT International Patent Application further describing the work of Looyestijn and his colleagues (WO 97/34166 of R. Bonnie, M. Johannes, P. Hofstra, W. Looyestijn, , R. Sandor and J. Karl), there is disclosed a technique for determining the fraction of a fluid selected from at least two fluids in a formation that includes the following steps: selecting a relationship between the NMR echo response from the fluids, the fractions of the fluids, and at least one variable which affects the NMR echo response in a manner dependent on the fractions of the fluids, varying the at least one variable, such as wait time or pulse spacing, in the course of an NMR measurement to thereby affect the NMR echo response in a manner dependent on the fractions of the fluids, and determining the fraction of the selected fluid by fitting the NMR echo response to the selected relationship. An example set forth in WO 97/34166 involves the determination of water saturation in a rock formation containing a medium gravity oil and water by applying a gradient magnetic field NMR measurements on a sample of the rock formation. The water was modeled with two transverse relaxation times and two corresponding volume fractions, the component with the short relaxation time representing bound water and the component with the long relaxation time representing movable water. The oil was modeled by one transverse relaxation time and one corresponding volume fraction. The WO 97/34166 Publication states that by repeating their method for a range of practical values for the water and oil parameters, it was found that the method according to their invention is only weakly dependent on the actual values of the oil parameters. If no information on these parameters is available, the Publication states that errors in estimated water saturation may be up to 0.1. It further states that if the oil viscosity can be estimated at an accuracy of two decimals, the resulting error in water saturation is negligible compared to the overall accuracy of the measurement. Thus, in this technique, which models oil with one transverse relaxation time with a corresponding volume fraction, prior knowledge of oil viscosity is apparently needed to obtain adequate accuracy. In well logging practice, prior knowledge of the in situ oil viscosity is usually not known. The Bonnie, et al. technique further requires an input for the brine T1/T2 ratio. This quantity is variable and unknown so that a proper value cannot be generally input. The result of inaccuracies in the input T1/T2 ratio can lead to errors in the fluid amplitudes estimated by this technique. In summary, the prior methods lack a coherent theoretical and operational framework needed to provide an accurate and complete NMR based formation evaluation. It is among the objects of the present invention to provide an improved formation evaluation technique that overcomes limitations of prior art techniques.

SUMMARY OF THE INVENTION

A feature of the present invention is the introduction into an inversion processing technique of a model having crude oils with a distribution of constituent viscosities. The constituent viscosities can be directly related to the distribution of NMR relaxation times measured on bulk crude oil samples and reflect the complex composition of crude oils as a mixture of many different types of hydrocarbon molecules. The constituent viscosities simplify the inversion by providing a single set of parameters for characterizing the crude oil distributions of bulk relaxation times and diffusion constants. It is shown that the macroscopic viscosity of the crude oil can be expressed as the logarithmic mean of the distribution of constituent viscosities. It is also shown theoretically in Appendix B hereof why there also exists in crude oils a distribution of diffusion constants. Moreover, it is predicted that the diffusion constant and relaxation time distributions in crude oils have similar character.

In accordance with a form of the invention, there is set forth a method for determining properties of earth formations surrounding a borehole, comprising the following steps: (a) providing a logging device that is moveable through the borehole; (b) transmitting electromagnetic energy from the logging device into the formations, and receiving nuclear magnetic resonance spin echoes at the logging device; (c) performing step (b) a plurality of times, with a respective plurality of different transmitting and/or receiving conditions to obtain a plurality of measurements; (d) generating a formation model that includes a plurality of model components for a brine phase and a plurality of model components for a native oil phase; (e) modifying the model components to optimize the model with respect to the measurement signals; and (f) outputting model components of the optimized model.

Depending on the circumstances, the step (d) of generating a formation model can include generating a model that further includes an oil base mud filtrate component and/or can include a gas component.

In an embodiment of the invention, the step of transmitting electromagnetic energy from the logging device and receiving nuclear magnetic resonance spin echoes at the logging device includes producing a static magnetic field in a region of investigation and generating sequences of magnetic field radio frequency pulses in the region of investigation and receiving sequences of nuclear magnetic resonance spin echoes. In this embodiment, the applied static magnetic field gradient in the investigation region is $G_p$, the wait time between sequences is $W_p$, the echo spacing is $TE_p$, and the number of received spin echoes of a sequence is $J_p$, and the above step (c) comprises performing step (b) a plurality of times with respective different values of at least one condition selected from the group consisting of $G_p$, $W_p$, $TE_p$ and $J_p$. Also in this embodiment, the step (c) comprises performing step (b) N times to obtain a suite of N measurements, and the measurements p are taken at a plurality of respectively separate measurement region shells in the formations. The individual shells being investigated can be frequency selected by the logging device.

In an embodiment of the invention, the step (d) of generating a formation model includes generating a set of model amplitude components that define the transverse relaxation time distribution of the brine phase, and a further set of model amplitude components that define the transverse relaxation time distribution of the native oil, and a further set of model components that define the constituent viscosities of the native oil.

The technique hereof provides improvements in all of the standard NMR answer products, including estimates of total NMR porosity, free-fluid and bound-fluid porosity, $T_2$-distributions and permeability in shaly sands. In addition, it can provide estimates of water, oil, OBMF, and gas filled porosities and saturations, oil viscosity, oil $T_1$-distributions, oil diffusion constants, and brine $T_1/T_2$ ratios. Fluid saturation profiles can also be obtained.

The technique hereof can also be applied to measurements taken above ground on core samples of earth formations. In such case, the core sample can be placed in NMR laboratory equipment (or on the logging tool itself), and an appropriate pulse sequence and echo collection can be implemented. The fluid volumes in the core and the other formation evaluation parameters provided by the technique can be determined.

Further features and advantages of the invention will become more readily apparent from the following detailed description when taken in conjunction with the accompanying drawings.

DETAILED DESCRIPTION

Figures 1, 2:
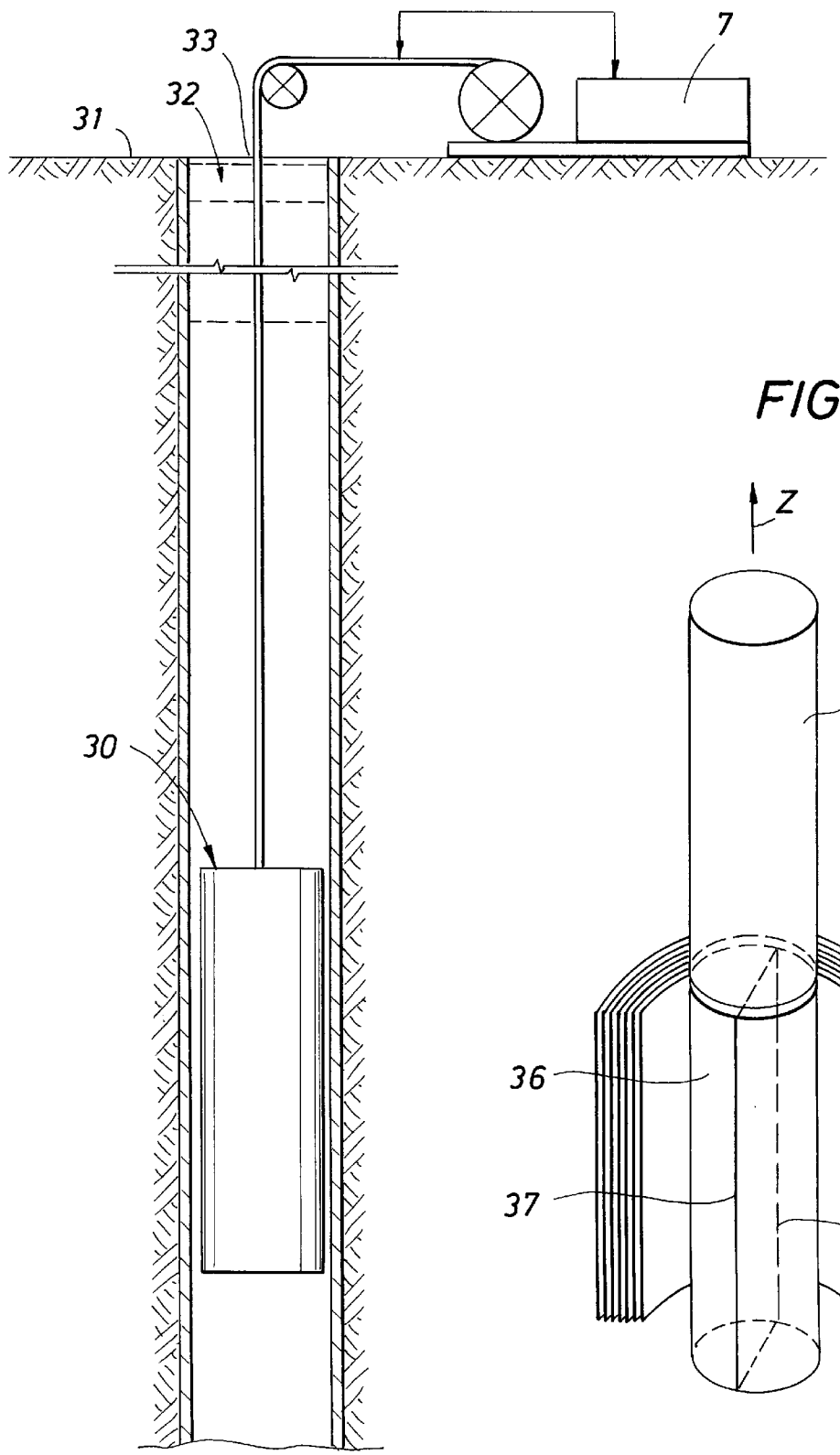
FIG. 1 is a diagram, partially in block form, of an apparatus that can be used in practicing an embodiment of the present invention.
FIG. 2 is a diagram of a type of logging device of the FIG. 1 apparatus that can be used to obtain measurements employed in an embodiment of the invention.

Referring to FIG. 1, there is shown an apparatus for investigating subsurface formations 31 traversed by a borehole 32, which can be used in practicing embodiments of the method of the invention.

An investigating apparatus or logging device 30 is suspended in the borehole 32 on an armored cable 33, the length of which substantially determines the relative depth of the device 30. The cable length is controlled by suitable means at the surface such as a drum and winch mechanism (not shown). Surface equipment, represented at 7, can be of conventional type, and can include a processor subsystem and communicates with the downhole equipment.

The logging device which makes the measurements can be any suitable nuclear magnetic resonance logging device, for use in wireline logging applications as shown, or of a type that can be employed in measurement while drilling applications. The device 30 includes, for example, a means for producing a static magnetic field in the formations, and radio frequency (RF) antenna means for producing pulses of RF magnetic field in the formations and for receiving the spin echoes from the formations. The means for producing a static magnetic field can comprise for example a permanent magnet or magnet array, and the RF antenna means for producing pulses of RF magnetic field and receiving spin echoes from the formations can comprise for example one or more RF antennas. An embodiment of the invention utilizes a suite of measurements from an NMR logging device of a type that can be operated to obtain separate measurements from a plurality of closely spaced thin shell regions in the surrounding formations. A simplified representation of some of the components of a suitable type of logging device 30 is illustrated in FIG. 2. The Figure shows a first centralized magnet or magnet array 36 and an RF antenna, represented at 37, which can be a suitably oriented coil or coils. FIG. 2 also illustrates a general representation of the type of closely spaced cylindrical thin shells, 38-1, 38-2. . .38-N, that can be frequency selected using the referenced type of multifrequency logging device. As is known in the art, for example as disclosed in U.S. Pat. No. 4,710,713, the logging device can select the shell region to be investigated by appropriately selecting the frequency of the RF energy in the transmitted pulses. In FIG. 2, a further magnet or magnet array is represented at 39, and can be utilized for applying a pre-polarizing static magnetic field to formations being approached by the investigating region of the logging device as it is raised in the borehole in the direction of arrow Z. Reference can be made, for example, to U.S. Pat. No. 5,055,788. Also see U.S. Pat. No. 3,597,681.

Figure 3:
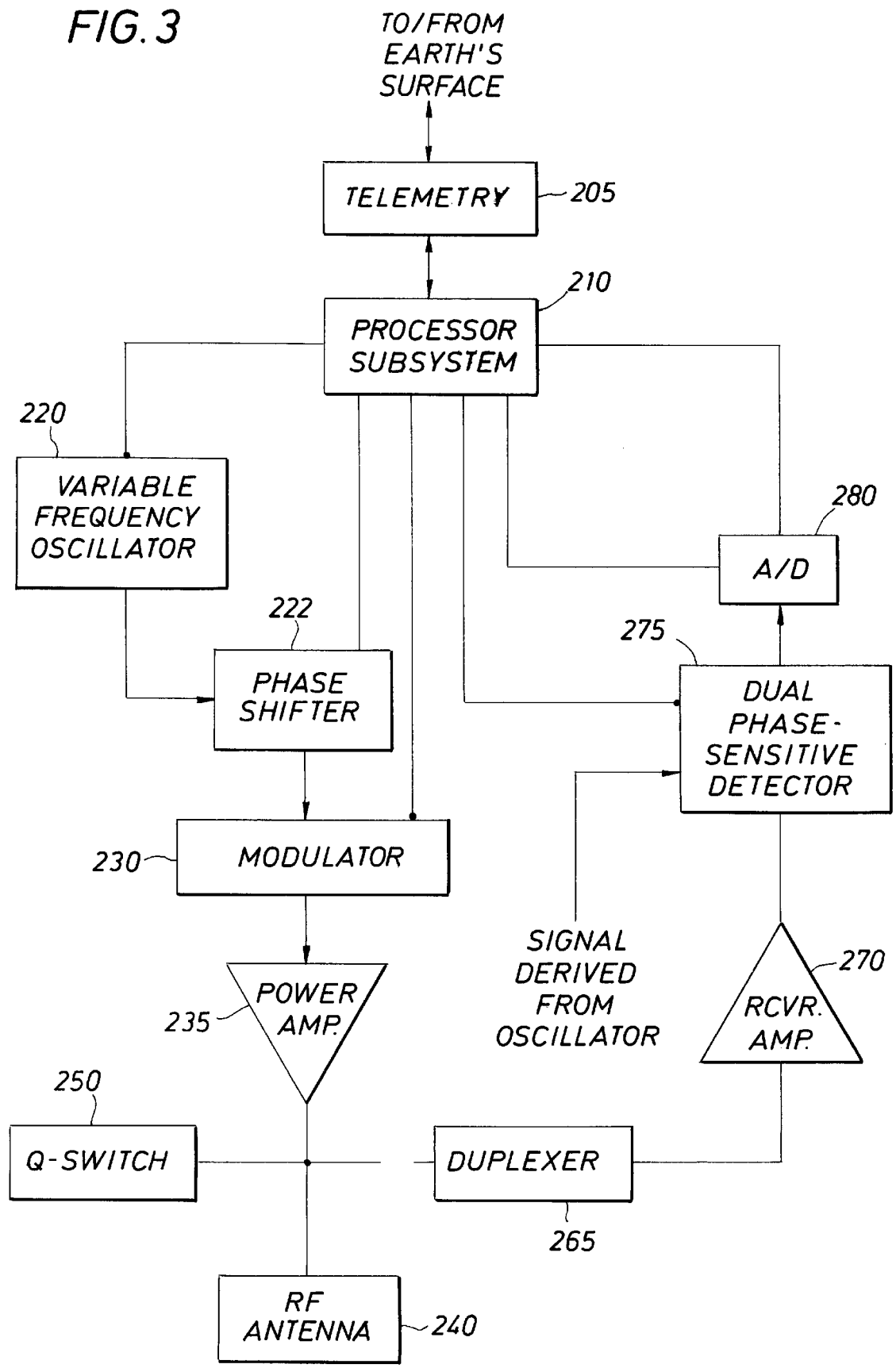
FIG. 3 shows, in simplified form, circuitry of known type for producing the RF pulses and for receiving and storing the spin echoes.

FIG. 3 shows, in simplified form, circuitry of known type for producing the RF pulses and for receiving and storing the spin echoes. It will be understood that any other suitable circuitry could be used in practicing the technique hereof.

In the Figure diagram, a downhole processor subsystem is represented at 210. The processor subsystem 210 has associated memory, timing, interfaces, and peripherals (not separately shown), as is well known in the art. The processor subsystem is conventionally coupled with telemetry circuitry 205, for communication with the earth's surface. The pulse forming circuitry includes a variable frequency oscillator 220 which produces radio frequency (RF) signals at the desired frequencies under control of the processor, and the output of the oscillator is coupled to a phase shifter 222 and then to a modulator 230, both of which are under control of the processor subsystem 210. The phase shifter and modulator can be controlled, in a manner known in the art, to produce the desired pulses of RF field, for example the 90 degree and 180 degree pulses for CPMG types of sequences or any other desired NMR pulse sequences. The output of modulator 230 is coupled, via a power amplifier 235, to the RF antenna 240. A Q-switch 250 can be provided to critically damp the RF antenna system to reduce antenna ringing. The antenna 240 is also coupled with a receiver section via duplexer 265, the output of which is coupled to receiver amplifier 270. The duplexer 265 protects the receiver amplifier 270 from the high power pulses which pass to the RF antenna 240 during the transmitting and damping modes. During the receiving mode, the duplexer 265 is effectively just a low impedance connection from the antenna to the receiver amplifier 270. The output of the receiver amplifier 270 is coupled to a dual phase-sensitive detector 275, which also receives, as a reference, a signal derived from the oscillator signal. The detected output is coupled to analog-to-digital converter 280, the output of which is a digital version of the received nuclear magnetic resonance signal. Although the logging device or tool 30 is shown as a single body in FIG. 1, it may alternatively comprise separate components, and the tool may be combinable with other logging tools. Also, while a wireline is illustrated, alternative forms of physical support and communicating link can be used, for example in a measurement while drilling system.

In the described embodiment the shells within a band are closely spaced (e.g., of the order of 10 millimeters) so that the fluid saturation can be assumed constant over the extent of the band. N measurements are made within a band of shells. Each measurement is characterized by a parameter set $\{W_p, TE_p, G_p, J_p\}$ for p=1, N where $W_p$ is the wait time (s), $TE_p$ is the echo spacing (s), $G_p$ is the applied static magnetic field gradient (Gauss/cm), and $J_p$ is the number of spin-echoes acquired. Each measurement is assumed to be distinct so that if a measurement is repeated, then it is "stacked" (averaged with its counterparts, for noise reduction). With this convention no two measurement parameter sets are identical.

NMR Multi-fluid Relaxational Model

Figure 4:
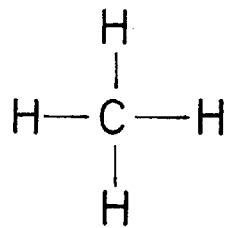
FIG. 4 is a diagram illustrating the molecular structure of some components of a typical crude oil.
Figure 4:
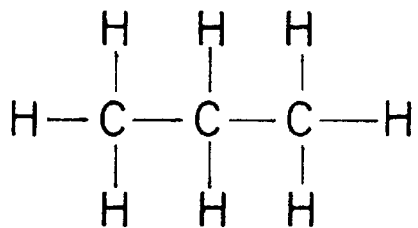
Figure 4:
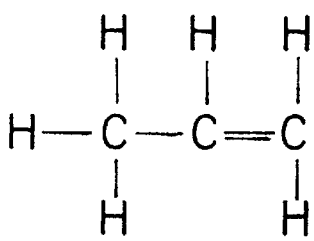
Figure 4:
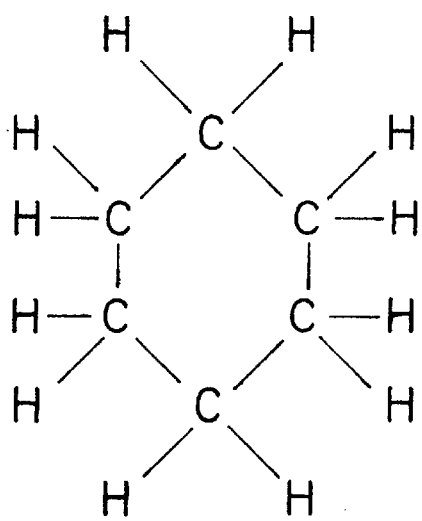
Figure 4:
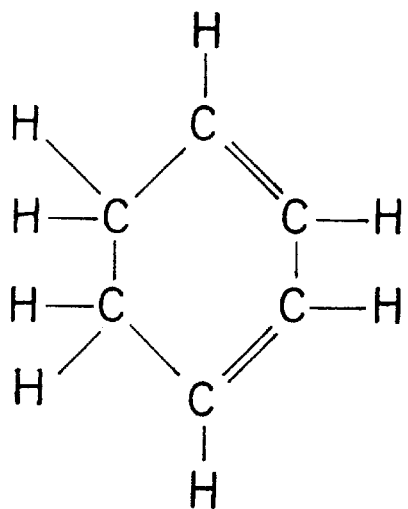
Figure 5A:
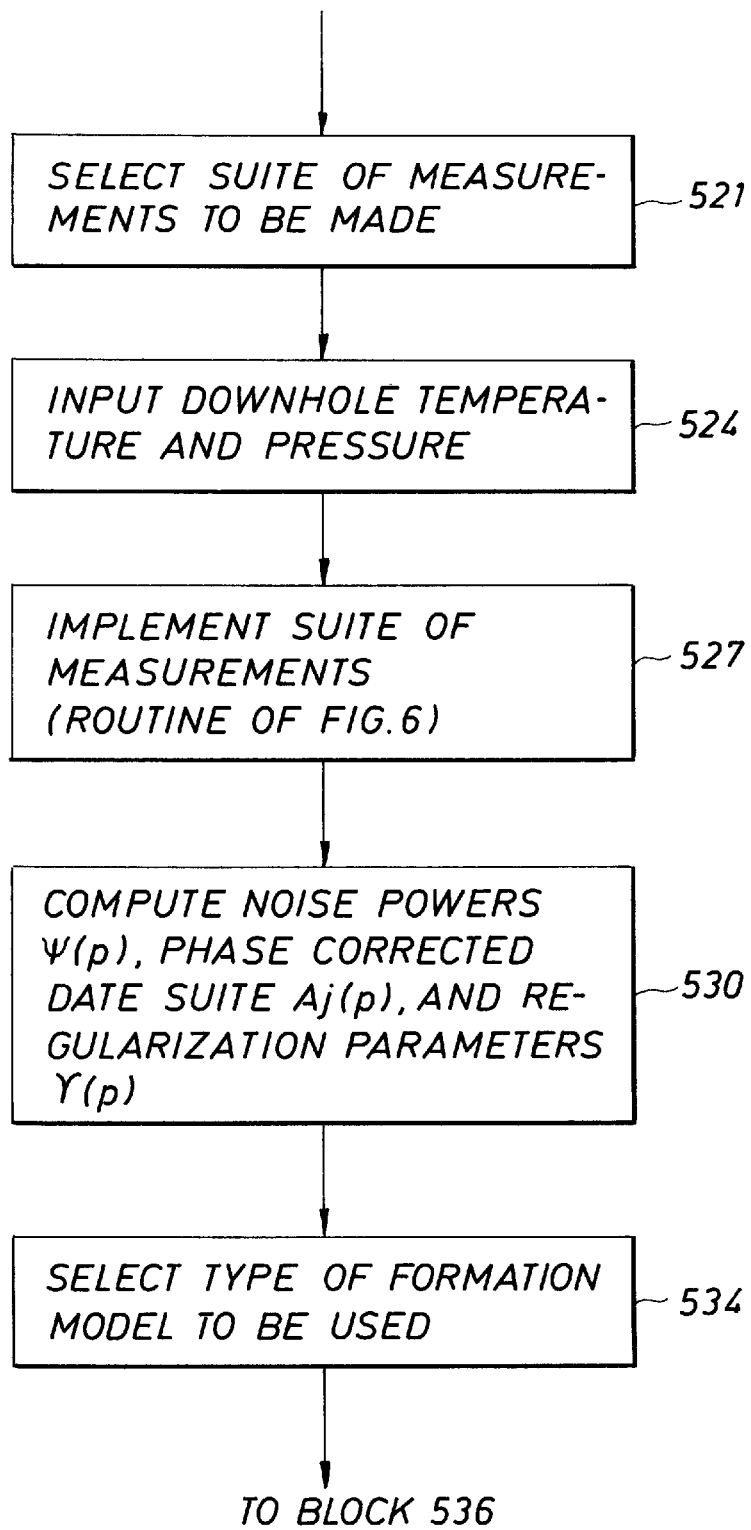
FIG. 5, which includes FIGS. 5A, 5B, 5C, 5D, 5E, and 5F, placed one below another, is a flow diagram of a routine for controlling a processor in accordance with an embodiment of the present invention.
Figure 5B:
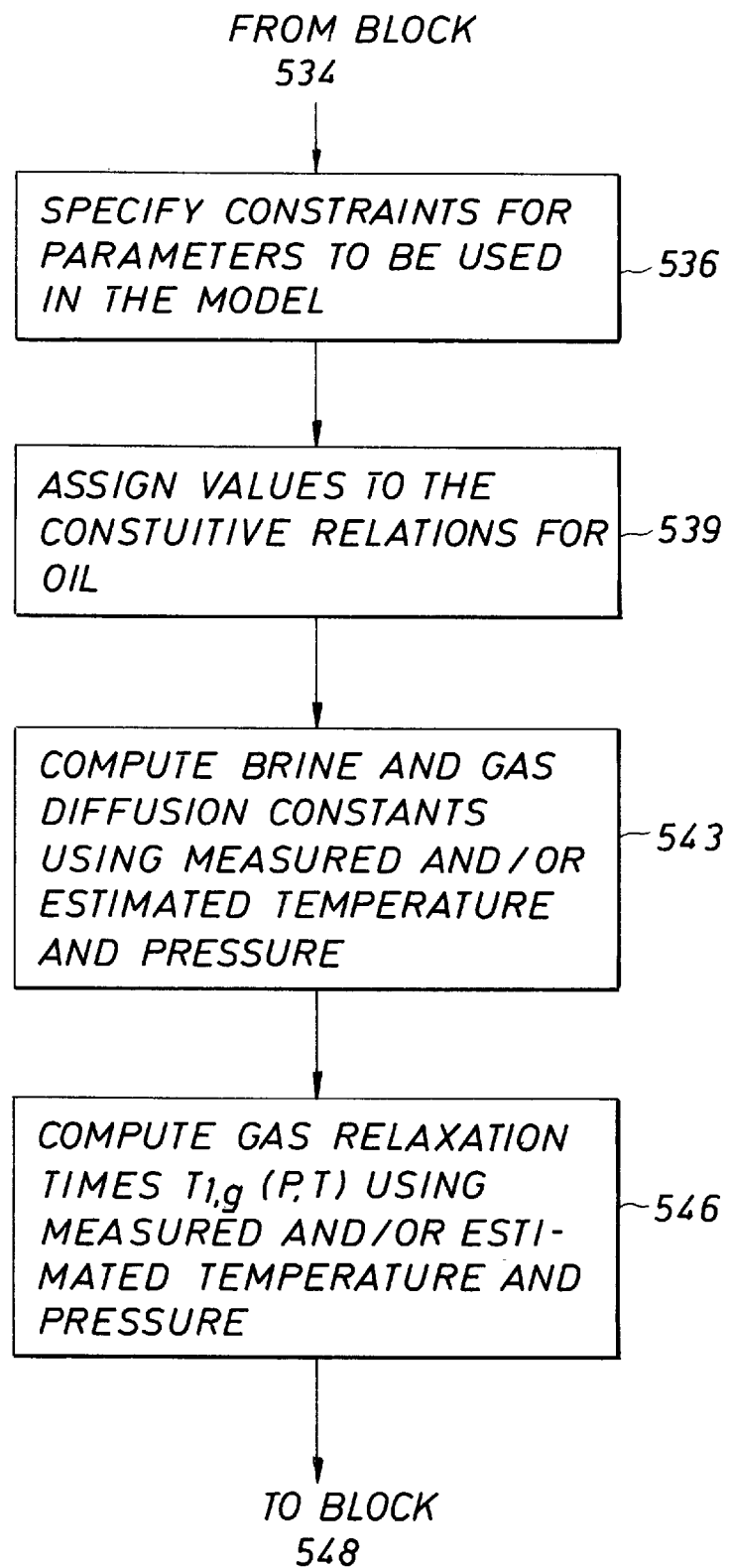
Figure 5C:
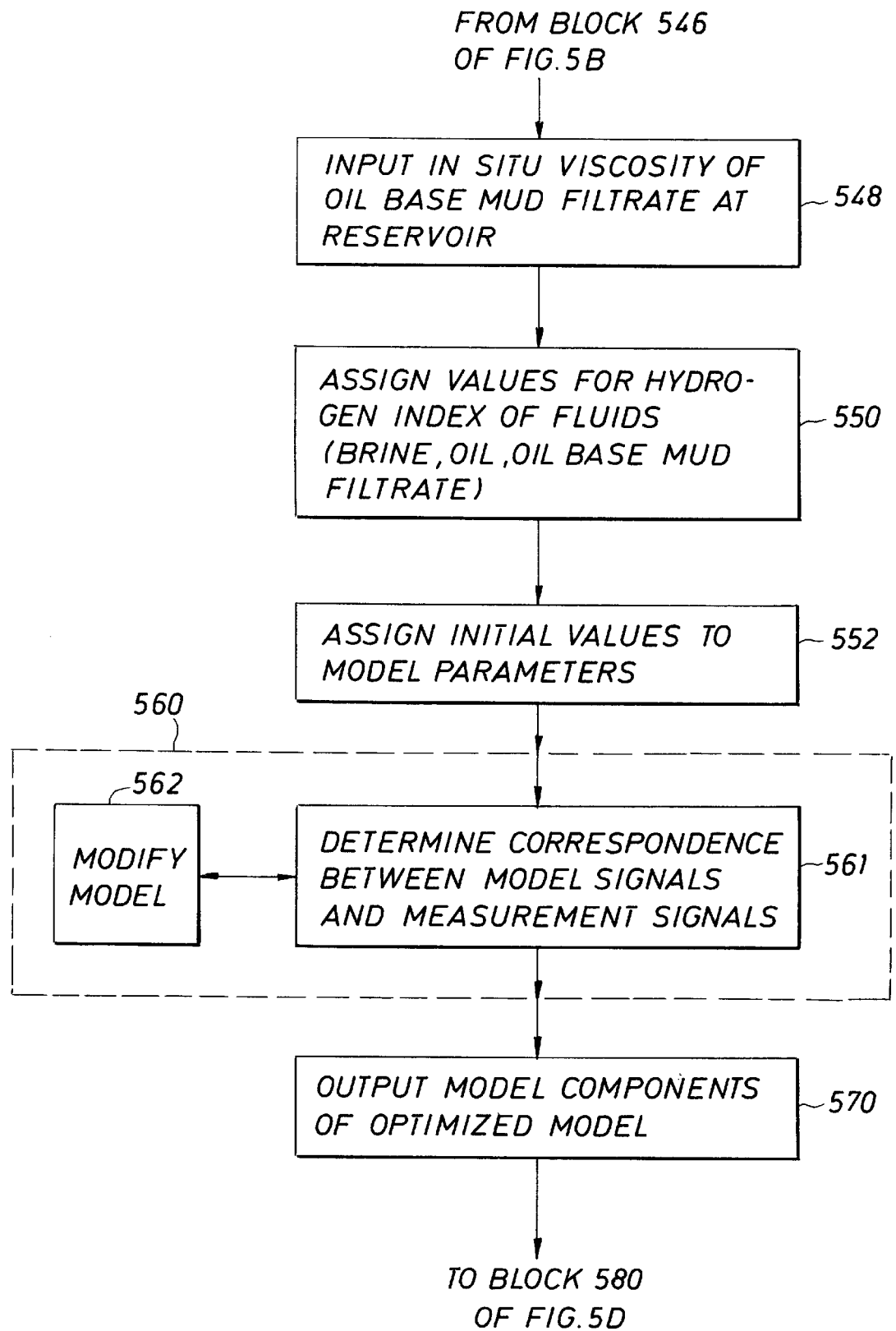
Figure 5D:
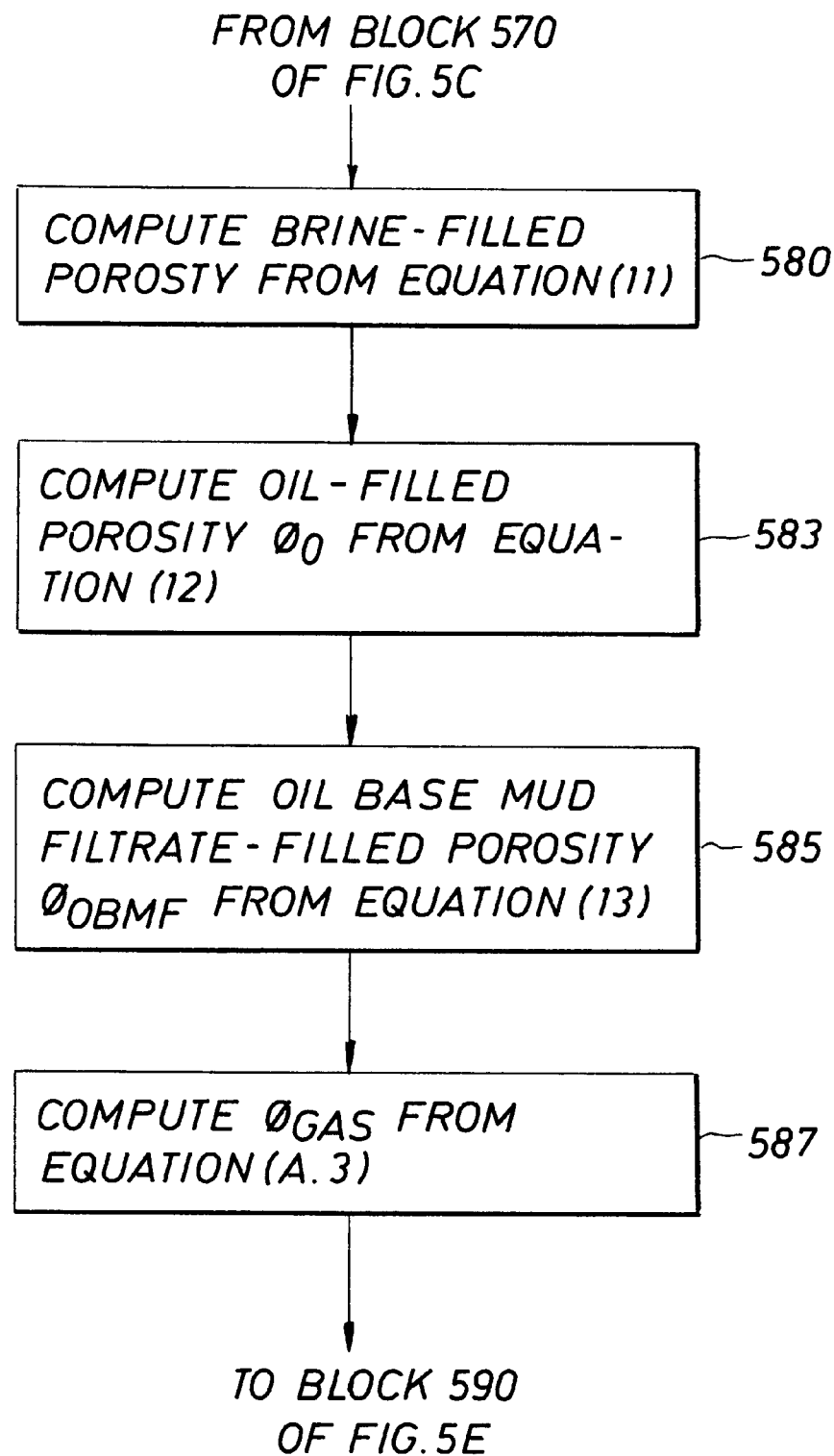

Consider a general spin echo relaxation model for a formation containing brine and native oil. Because many wells are drilled with oilbase muds, the model also allows for the presence of oilbase mud filtrate (OBMF) in the formation. In the Appendix A the model is extended to include gas. Let $A_j^p$ represent the amplitude of the j-th echo acquired during measurement p. Consider the following general relaxation model, $$A_j^p = \sum_{l=1}^{N_s} a_l \exp\left(-\frac{j*TE_p}{T_{2,l}^\dagger(p)}\right)\left(1 - \exp\left(-\frac{W_p}{\xi * T_{2,l}}\right)\right) + \sum_{k=1}^{N_o} b_k \exp\left(-\frac{j*TE_p}{T_{2,o}^\dagger(\eta_k, p)}\right)\left(1 - \exp\left(-\frac{W_p}{T_{1,o}(\eta_k)}\right)\right) + A_{OBMF}\exp\left(-\frac{j*TE_p}{T_{2,OBMF}^\dagger(p)}\right)\left(1 - \exp\left(-\frac{W_p}{T_{1,OBMF}}\right)\right) \quad (1)$$

where the first, second and third terms are brine, native oil and OBMF signals, respectively. The model explicitly accounts for the experimentally observed distribution of brine and crude oil relaxation time distributions. Measurements on oil based mud filtrates show that the relaxation time distributions are very narrow and can be described by a single exponential. The apparent transverse relaxation rates include self diffusion of fluid molecules in the static magnetic gradient $G_p$ which for unrestricted diffusion in a uniform gradient can be written in the well known form, $$\frac{1}{T_{2,l}^\dagger(p)} = \frac{1}{T_{2,l}} + \frac{(\gamma_H * G_p * TE_p)^2}{12} D_w(T), \quad (2)$$

for the brine phase. The $T_{2,l}$, are a set of $N_s$ logarithmically spaced relaxation times that represent the sum of surface and bulk relaxation of the brine phase. The second term on the right hand side is the contribution to the relaxation rate from diffusion where $\gamma_H = 2\pi*4258$ G$^{-1}$s$^{-1}$ is the proton gyromagnetic ratio and $D_w(T)$ is the temperature dependent self diffusion coefficient of water in units of cm$^2$/s. Corrections to $D_w(T)$ for the effects of restricted diffusion and to $G_p$ for the effects of internal rock gradients can be applied if appropriate (see Appendix E). The apparent relaxation rate of native oil can be written in the form, $$\frac{1}{T_{2,o}^\dagger(\eta_k, p)} = \frac{1}{T_{2,o}(\eta_k)} + \frac{(\gamma_H * G_p * TE_p)^2}{12} D_o(\eta_k), \quad (3)$$

where $T_{2,o}(\eta_k)$ is the bulk relaxation time associated with amplitude $b_k$ in the native oil relaxation time distribution and $D_o(\eta_k)$ is a viscosity dependent diffusion constant. The crude oil is usually assumed to be a non-wetting phase that is not affected by surface relaxation. It is postulated that in crude oils there exist on a molecular level a distribution of constituent viscosities ($\eta_k$), and this postulate is consistent with experimental data that there exists a distribution of relaxation times in crude oils. Morriss, et al. (Hydrocarbon Saturation And Viscosity Estimation From NMR Logging In The Belridge Diatomite, Paper C presented at the 35$^{th}$ Annual Meeting Of The Society Of Professional Well Logging Analysis, 1994) showed, for a suite of crude oils, that there exists a strong correlation between the logarithmic mean relaxation times of their distributions and their measured viscosities. The measured viscosity is a macroscopic transport property of the crude oil that determines its flow properties and is the quantity that is used in hydrodynamic transport equations like the Navier-Stokes equation. The $\eta_k$ in Eq. (3) are phenomenological microscopic variables that reflect the complex composition of crude oils. Crude oils are mixtures consisting of many different types of hydrocarbon molecules of varying sizes, shapes and molecular weights (McCain, W. D., The Properties Of Petroleum Fluids, published by Penn Well Publishing Co., Second Edition, Chapter 1, 1990). FIG. 4 shows a few components that might be present in a typical crude oil.

The macroscopic viscosity ($\eta_o$) of crude oils is empirically related to the logarithmic mean (($\overline{T}_{2,o})_{log}$) of the transverse relaxation time distributions by a constitutive equation of the form, $$\frac{1}{(\overline{T}_{2,o})_{logm}} = \frac{a\eta_o}{T} \equiv c\eta_o(s^{-1}), \quad (4)$$

where a≅250 is an empirically determined constituent constant given by Looyestijn (Determination Of Oil Saturation From Diffusion NMR Logs, Paper SS presented at the 37$^{th}$ Annual Meeting of the Society of Professional Well Log Analysts, 1996), T the temperature in degrees Kelvin, and c≡aT$^{-1}$. In analogy with the above equation assume that the constituent viscosities are related to the components in the relaxation time distribution via the same equation, $$\frac{1}{T_{2,o}(\eta_k)} = \frac{a\eta_k}{T} \equiv c\eta_k. \quad (5)$$

The dependence of the relaxation times in (4) and (5) on viscosity and temperature are consistent with the experiments and theoretical predictions of the pioneering work of Bloembergen, Purcell, and Pound (Relaxation Effects In Nuclear Magnetic Resonance Absorption, Physical Review, v. 73, no 7, pp. 679–712, 1948) Using the definition of the logarithmic mean relaxation time, $$(\overline{T}_{2,o})_{logm} = 10^{\sum_{k=1}^{N_o} \overline{b}_k \log(T_{2,o}(\eta_k))}, \quad (6)$$

with, $$\overline{b}_k = \frac{b_k}{\sum_{k=1}^{N_o} b_k}, \quad (7)$$

where the $b_k$ are the $N_o$ amplitudes in the crude oil bulk relaxation time distribution. If (4) and (5) are substituted into (6) one finds that the macroscopic viscosity of the crude oil is the logarithmic mean of the $\eta_k$, i.e., $$\eta_o = 10^{\sum_{k=1}^{N_o} \bar{b}_k \log(\eta_k)}, \quad (8)$$

which is similar to the high temperature limit of the "Arrenhius mixing rule" for the viscosity of a mixture (see Bondi, A., Physical Properties Of Molecular Crystals, Liquids, And Glasses, published by John Wiley & Sons. pp. 348–349, 1968), where $\bar{b}_k$ is the "concentration" of the mixture constituent with viscosity nk. An important difference between the viscosity mixing rule in equation (8) and the Arrenhius mixing rule is that the $\eta_k$ in equation (8) are constituent viscosities in the mixture, and are not equal to the pure component viscosities. Thus, the postulate "that the empirically observed distribution of transverse relaxation times implies a distribution of constituent viscosities on the molecular level", when combined with the empirically established correlation in Eq. (4) leads to an Arrenhius type of mixing rule for the viscosity of a crude oil mixture. The distribution of constituent viscosities provides information on the compositions and molecular weights of the crude oil constituents. The macroscopic crude oil viscosity, in addition to determining the flow properties of the oil, can be related to its API gravity (Morriss, et al., 1994, supra).

The apparent transverse relaxation rate of the OBMF in Eq. (1) can be written in the form, $$\frac{1}{T_{2,OBMF}^\dagger(p)} = \frac{1}{T_{2,OBMF}} + \frac{(\gamma_H * G_p * TE_p)^2}{12} D_{OBMF}, \quad (9)$$

where $T_{2,OBMF}$ and $D_{OBMF}$ are the bulk relaxation time and self diffusion constant of the OBMF.

It is usually stated in the published literature that the transverse and longitudinal relaxation times of the bulk crude oil and OBMF (i.e., in zero magnetic field gradient) can be assumed to be equal so that in Eqs. (1) and (3), $T_{1,o}(\eta_k) = T_{2,o}(\eta_k)$ for native oil and in Eqs. (1) and (9), $T_{1,OBMF} = T_{2,OBMF}$ for the filtrate. Note that the assumption that the $T_1$ and $T_2$-distributions of crude oils are equal is not an essential ingredient since the relaxational model can be tailored to account for unequal distributions. In fact, recently acquired data in crude oils suggest to applicant that the $T_1$ and $T_2$ distributions in some crude oils can differ significantly and in those cases the $T_1|T_2$ ratios seem to be correlated with the asphaltene content of the oil.

For convenience of description, $\bar{\eta} = \eta * T^{-1}$ is defined as the ratio of viscosity to absolute temperature. The dependence on n of the bulk relaxation times of many liquids as given in Eqs. (4)–(5) has been experimentally verified by many experiments in a variety of systems (see Abragam, A., The Principles Of Nuclear Magnetism, published by Oxford Univ. Press, pp. 324–325, 1961; Zhang, Q., Lo, S-W., Huang, C. C., Hirasaki, G. J., Kobayashi, R., and House, W. V., Some Exceptions To Default NMR Rock And Fluid Properties, Paper FF presented at the 39$^{th}$ Annual Meeting of the Society of Professional Well Log Analysts, 1998). A log-log plot of mean relaxation time (e.g., $(\bar{T}_1)_{log\ m}$) versus $\bar{\eta}$ for many liquids including stock tank crude oils can be fit by a straight line with slope equal to −1. Zhang, et al. (1998, supra) show that the relaxation time in pure methane has the reciprocal dependence (slope equal to 1) on r that is observed in liquids and state that this is because relaxation is predominately by the spin-rotation mechanism in gas as opposed to dipole-dipole relaxation in liquids. Zhang, et al. further state that relaxation times of reservoir crude oils containing dissolved methane might deviate from the in $\bar{\eta}^{-1}$ dependence in Eqs. (4) and (5). They argue that a different functional dependence will be required to characterize the relaxation times of live oils. The relaxation times of live oils as functions of gas/oil ratio (GOR), temperature and viscosity have not to date been established, and are needed to augment or possibly even supplant the relationships assumed in Eqs. (4)–(5). The general relaxational model in Eq. (1) is still valid and only the functional dependence of relaxation time on viscosity and temperature might need to be modified. A recent publication by Lo, et al., (Relaxation Time And Diffusion Measurements of Methane And N-Decane Mixtures, The Log Analyst, pp. 43–46, November-December, 1998) show that in mixtures of methane and n-decane that a log—log plot of $T_1$ versus $\bar{\eta}$ deviates from a straight line (i.e, a simple power law dependence) as the mole fraction of gas in the mixture is increased. This suggests that for in-situ crude oils having high gas-oil ratios that a more general functional dependence of relaxation time on viscosity and temperature than expressed by Eqs. (4) and (5) is required. The results of Lo, et al. show that the gas/oil ratio (i.e., GOR) is an important parameter in determining the relaxation time dependence on viscosity and temperature. The functional dependence of the relaxation time on $\bar{\eta}$ for live crude oils will also deviate from a simple power law relationship—and will have an explicit dependence on the GOR.

It is further assumed that the self-diffusion constants $D_o(\eta_k)$ of the constituents of the crude oil in Eq. (3) have the same dependence on $\eta_k * T^{-1}$ as the relaxation times in Eq. (5). This dependence is predicted by the Einstein-Stokes diffusion theory and has been verified experimentally in many kinds of liquids (Abragam, 1961, supra). For crude oils, $$D_o = \frac{bT}{\eta_o} \times 10^{-5}, \quad (10)$$

where $D_o$ is the measured crude oil diffusion constant in cm$^2$/s and T is the temperature in degrees Kelvin. The empirical constitutive constant, $b \approx 25/300 = 8.33 \times 10^{-3}$, is given by Looyestijn (1996, supra). In analogy with Eq. (5), the constituent diffusion constants of crude oil mixtures are related to the constituent viscosities by the equations, $$D_o(\eta_k) = \frac{bT}{\eta_k} \times 10^{-5}. \quad (10a)$$

Equation (10a) implies that in a crude oil mixture there exists on a molecular level a distribution of diffusion constants analogous to the distribution of relaxation times. NMR is a local measurement that can probe a system on a molecular scale and NMR pulsed field gradient measurements have been used by Lo, et al., (1998, supra) to measure the distribution of diffusion constants in mixtures of methane and n-decane. The diffusion constant distribution found by Lo, et al. exhibits two distinct peaks as expected for a binary mixture of a gas and a liquid. Appendix B shows theoretically why there is a distribution of diffusion constants in the crude oil and also establishes a link between the $\eta_k$ in Eq. (10a) and the frictional force that opposes the motion of the k-th component in the crude oil mixture. Appendix C treats some alternative parameterizations of the relaxational model.

Parameters In The Relaxational Model To Be Determined By Inversion

The relaxational model in Eq. (1) defines a forward model to be inverted using data from a set of closely spaced measurements in a band of shells. Note that the shells are generally closely spaced to minimize differences in saturation from shell to shell that could be caused by drilling fluid invasion. If invasion is not a factor (e.g. for deep NMR measurements), then more widely spaced shells could be employed. The unknown parameters that are to be determined from the inversion in the present embodiment are: (1) the set of $N_s$ amplitudes $\{a_l\}$ that define the $T_2$-distribution of the brine phase, (2) $\xi$, the apparent $T_1/T_2$ ratio of the brine phase, (3) the set of $N_o$ amplitudes $\{b_k\}$ that define the $T_2$-distribution of the native crude oil, (4) the set of No constituent viscosities $\{\eta_k\}$ of the crude oil, and (5) $A_{OBMF}$, the amplitude of the OBMF signal. There are a total of $N_s+2*N_o+2$ unknowns. The relaxation time and viscosity of the OBMF are assumed known from lab measurements prior to logging, but if these data are unavailable then the OBMF viscosity can be treated as an additional unknown parameter in the relaxational model. In practice, even if lab measurements are available on the properties of OBMF filtrates there will exist uncertainties and it will be important to study the robustness of the inversion when the assumed OBMF properties are varied. In wells drilled with waterbase muds, the model and the inversion problem is simplified because the filtrate signal can be included in the brine signal and the term representing the OBMF signal in Eq. (1) can be dropped from the model.

Formation Evaluation Parameters and Information Obtained from the Inversion

The following formation evaluation parameters can be computed from the inversion of the relaxational model in the present embodiment. The brine-filled porosity, O., is computed from the summation, $$\phi_w = \frac{1}{HI_w}\sum_{l=1}^{N_s} a_l, \tag{11}$$

where it is assumed without loss of generality that the amplitudes in the relaxational model defined in Eq. (1) are in porosity units. The hydrogen index of the brine ($HI_w$) can be estimated from the salinity of the formation water (Kleinberg, R. L. and Vinegar, H. J., NMR Properties Of Reservoir Fluids, The Log Analyst, pp. 20–32, November–December, 1996). The oil-filled porosity, $\phi_o$, is given by $$\phi_o = \sum_{k=1}^{N_0} \frac{b_k}{HI_{o,k}} \cong \frac{1}{HI_o}\sum_{k=1}^{N_0} b_k, \tag{12}$$

and the OBMF filled porosity, $\phi_{obmf}$, is simply $$\phi_{obmf} = \frac{1}{HI_{obmf}} A_{OBMF}, \tag{13}$$

where $HI_o$, and $HI_{obmf}$ are the hydrogen indices of the crude oil and OBMF, respectively. Note that in Eq. (12) it has been assumed that the distribution of hydrogen indices of the components in the crude oil is narrow so that $HI_{o,k}=HI_o$ where $HI_o$ is the macrosopic or measured hydrogen index of the mixture.

The hydrogen index of gas free crude oils can be estimated from the API gravity and is close to one for oils with API gravities greater than 25 (Kleinberg and Vinegar, 1996, supra). The hydrogen index of OBMF can be either measured using NMR or computed from the known chemical formula, mass density, molecular weight and number of hydrogen nuclei in the chemical formula. Formulas for the hydrogen index of live oils as a function of temperature, pressure and GOR have been published by Zhang, et al., (1998, supra). The oil saturation, $S_o(r)$, at the DOI (depth of investigation) in the band of shells where the measurements are acquired is given by $$S_o(r) = \frac{\phi_o}{\phi_w + \phi_o + \phi_{obmf}} \equiv \frac{\phi_o}{\phi_T} \tag{14}$$

where the defined total fluid filled porosity is $\phi_T$.

An "oil saturation profile" can be computed by making measurements in several bands at different DOI of closely spaced shells. The constraint of closely spaced shells at each DOI allows measurements on different shells to be combined with the assumption that the fluid saturations (and therefore the brine, crude oil and OBMF amplitudes in Eq. (1) ) do not vary significantly for measurements made on different shells within a band.

The macroscopic viscosity $\eta_o$ of the crude oil can be computed from the logarithmic mean of the $N_o$ constituent viscosities $\{\eta_k\}$ using Eq. (8). The $T_2$-distribution of the bulk oil can be computed from the $\{\eta_k\}$ using Eq. (5).

The brine $T_2$-distribution, a plot the $N_s$ amplitudes $\{a_l\}$ versus the logarithmically spaced times $T_{2,l}$ in Eq. (2), provides information on pore size distribution in formations where bulk brine relaxation is negligible compared to surface relaxation. This includes almost all shaly sand formations. The bound-fluid porosity can be computed by integrating the brine $T_2$-distribution from the $T_2$-sensitivity limit (minimum detectable $T_2$) to the bound-fluid cutoff, e.g., a value of 33 ms is commonly used in shaly sands. The bound-fluid porosity is important for predicting reservoir producibility and for estimating permeability. An attractive feature of the relaxation model in Eq. (1) is that the fluid signals are explicitly separated (even when they overlap in $T_2$-space) whereas in previously used models there was a single distribution function. Inversion of relaxation models that use a single distribution in a hydrocarbon zone, can lead to computation of erroneously high bound-fluid estimates for viscous oils (e.g., $T_{2,o}$ less than 33 ms) and also for light hydrocarbons when their apparent relaxation times are reduced by diffusion to less than the bound-fluid cutoff. Using a relaxation model that explicitly separates the fluids enables one to keep track of the bound-fluid which should normally appear only as part of the brine distribution.

The apparent $T_1/T_2$ ratio $\xi$ of the brine phase is an important ingredient in the inversion. It makes an automatic "polarization correction" to the brine amplitudes (reference can be made to copending U.S. Patent Application Ser. No. 09/156,417, filed Sep. 18, 1998, and assigned to the same assignee as the present application). This is especially important for measurement parameter sets that use pulse sequences acquired with short wait times. This feature of the inversion is necessary to insure that accurate values of total porosity ($\phi_T$) are computed. The use of measurements with short wait times is necessary to provide: (1) maximum $T_1$-sensitivity in reservoirs with medium to heavy viscosity oil, and (2) increased signal-to-noise ratio (SNR) from stacking many fast acquisitions.

Inversion of the Model

In the present embodiment, the inversion of the relaxation model in Eq. (1) is based on the Window Processing (WP)

method disclosed in U.S. Pat. No. 5,291,137 (see also above-referenced U.S. patent application Ser. No. 09/156, 417). This method has proven to be a robust, flexible, and fast inversion technique that is ideally suited for inversion of the non-linear relaxational model in Eq. (1). In the WP method a maximum likelihood functional of the unknowns (parameters) in the model is derived. The negative logarithm of the likelihood functional can be written in the form, $$-\ln L(\vec{x}) = \sum_{p=1}^{N} \left[ \sum_{m=1}^{N_w(p)} \frac{(\tilde{I}_m^p - I_m^p(\vec{x}))^2}{2\Psi_p \hat{\sigma}_{m,p}^2} + \frac{\gamma_p}{2\Psi_p} \left( \sum_{l=1}^{N_s} a_l^2 + \sum_{k=1}^{N_o} b_k^2 \right) \right], \quad (15)$$

where the elements of the vector x are the unknown parameters in the relaxational model.

The outer summation over p extends over all measurements within a band of shells and applies to all terms within the brackets. For each measurement p the inner sum is over a set of $N_w(p)$ pre-determined windows of residuals in the time domain. The number of windows $N_w(p)$ depends on the index p of the measurement parameter set because the number of windows depends on the number of spin echoes ($J_p$). The residuals in the m-th window are differences between the measured window sums ($\tilde{I}_p^m$) and the model windows sums ($I_p^m(\vec{x})$) computed from the relaxational model. The window sums are sums of echo amplitudes over time windows with the early time echoes being individually windowed to preserve sensitivity to fast relaxation times. The residuals for measurement p are weighted by the inverse measurement variances, i.e., $\psi_p$ is the noise variance on a single echo and $\hat{\sigma}_{m,p}^2 = N_{m+1,p} - N_{m,p} + \delta_{m,1}$ is the number of echoes in the window m where the integers $N_{m,p}$ and $N_{m+1,p}$ are the left and right endpoints (echo numbers) of the window. The delta function, $\delta_{m,1}$, is used to satisfy the window processing convention (U.S. Pat. No. 5,291,137, supra) that the first window contains its left hand endpoint. The last two summations over the squared amplitudes of the brine and crude oil $T_2$-distributions are minimum norm regularization or smoothing terms used to prevent noise artifacts in the inverted distributions. The regularization parameters ($\gamma_p$) are determined from the data for each measurement. The model window sums are summations over time windows of the echo amplitudes in Eq. (1) and can be written in the form:

$$I_m^p(\vec{x}) = \sum_{l=1}^{N_s} a_l F_{m,p}\left(\frac{TE_p}{T_{2,l}^\dagger(p)}\right)\left(1 - \exp\left(-\frac{W_p}{\xi T_{2,l}}\right)\right) + \sum_{k=1}^{N_o} b_k F_{m,p}\left(\frac{TE_p(c\eta_k^2 + d_p)}{\eta_k}\right)(1 - \exp(-W_p c\eta_k)) + A_{OBMF} F_{m,p}\left(\frac{TE_p}{R_{l,OBMF}^\dagger(p)}\right)\left(1 - \exp\left(-\frac{W_p}{T_{l,OBMF}}\right)\right) \quad (16)$$

where there have been introduced the sensitivity functions $F_{m,p}(y)$ which are defined by the summations of echoes over windows, $$F_{m,p}(y) = \sum_{j=N_{m,p}+\rho_m}^{N_{m+1,p}} \exp(-j*y), \quad (17)$$

The binary function, $\rho_m = 1 - \delta_{m,1}$, is used to satisfy the window processing convention (U.S. Pat. No. 5,291,137, supra) that only the first window contains its left hand endpoint. The geometric series in Eq. (17) can be summed to obtain a closed form for $F_{m,p}(y)$, i.e., $$F_{m,p}(y) = \frac{\exp(-y)}{\exp(-y) - 1}[\exp(-N_{m+1,p} y) - \exp(-(N_{m,p} + \rho_m - 1)y)]. \quad (18)$$

The arguments of the sensitivity functions in Eq. (16) are the ratios of the echo spacing to the apparent transverse relaxation times. Note that Eqs. (3), (5) and (10) have been used to write the crude oil apparent relaxation time in terms of the constituent viscosities, e.g., $$T_{2,0}^\dagger(\eta_k, p) = \frac{\eta_k}{c\eta_k^2 + d_p}, \quad (19)$$

where there has been defined, $$d_p = \frac{(\gamma_H G_p TE_p)^2}{12} bT \times 10^{-5}. \quad (20)$$

Analytical Derivatives for the Inversion

The robustness of the constrained minimization of Eq. (15) is facilitated by the use of analytical derivatives for all of the parameters. The constraints on the parameter estimates are upper and lower bounds. The minimization should be performed using double precision. At the minimum these derivatives should be numerically zero except for a solution that is on a boundary. The analytical expressions for the derivatives are given below. The derivatives with respect to the brine spectral amplitudes are given by, $$-\frac{\partial \ln L(\vec{x})}{\partial a_k} = \sum_{p=1}^{N} \left[ -\left\{ \sum_{m=1}^{N_w(p)} \frac{(\tilde{I}_m^p - I_m^p(\vec{x}))}{\Psi_p \hat{\sigma}_{m,p}^2} F_{m,p} \right. \right. \left. \left( \frac{TE_p}{T_{2,k}^\dagger} \right)\left(1 - \exp\left(-\frac{W_p}{\xi T_{2,k}}\right)\right) \right\} + \frac{\gamma_p a_k}{\Psi_p} \right], \quad (21)$$

for $k=1, \ldots, N_s$. The derivative with respect to $\xi$, the brine apparent $T_1/T_2$ ratio is $$-\frac{\partial \ln L(\vec{x})}{\partial \xi} = \xi^{-2} \sum_{p=1}^{N} W_p \sum_{m=1}^{N_w(p)} \frac{(\tilde{I}_m^p - I_m^p(\vec{x}))}{\Psi_p \hat{\sigma}_{m,p}^2} S_{m,p}(\xi), \quad (22)$$

where the matrix function $S_{m,p}(i)$ is defined by $$S_{m,p}(\xi) = \sum_{l=1}^{N_s} \frac{a_l}{T_{2,l}} F_{m,p}\left(\frac{TE_p}{T_{2,l}^\dagger}\right) \exp\left(-\frac{W_p}{\xi T_{2,l}}\right). \quad (23)$$

The derivatives with respect to the crude oil spectral amplitudes are given by, $$-\frac{\partial \ln L(\vec{x})}{\partial b_k} = \sum_{p=1}^{N}\left[-\left\{\sum_{m=1}^{N_w(p)}\frac{(\tilde{I}_m^p - I_m^p(\vec{x}))}{\Psi_p \hat{\sigma}_{m,p}^2}F_{m,p}\right.\right. \qquad (24)$$

$$\left.\left.\left(\frac{TE_p(c\eta_k^2 + d_p)}{\eta_k}\right)(1-\exp(-W_p c\eta_k))\right\} + \frac{\gamma_p b_k}{\Psi_p}\right],$$

for $k=1,\ldots,N_o$. The derivatives with respect to the crude oil constituent viscosities are given by, $$-\frac{\partial \ln L(\vec{x})}{\partial \eta_k} = -\sum_{p=1}^{N}\sum_{m=1}^{N_w(p)}\frac{(\tilde{I}_m^p - I_m^p(\vec{x}))}{\Psi_p \hat{\sigma}_{m,p}^2} \qquad (25)$$

$$\left[b_k W_p c F_{m,p}\left(\frac{TE_p(c\eta_k^2 + d_p)}{\eta_k}\right)\right.$$

$$\exp(-W_p c\eta_k) + b_k F'_{m,p}\left(\frac{TE_p(c\eta_k^2 + d_p)}{\eta_k}\right)$$

$$\left.\left(\frac{TE_p(c\eta_k^2 - d_p)}{\eta_k^2}\right)(1-\exp(-W_p c\eta_k))\right],$$

for $k=1,\ldots,N_o$. In the above equation $F_{m,p}'(y)$ is the derivative of the sensitivity function $F_{m,p}(y)$ in Eq. (18) with respect to its argument, i.e., explicitly, $$F'_{m,p}(y) = \frac{1}{(\exp(-y)-1)^2}[(A_{m,p}-1)\exp(-(A_{m,p}+1)y) - \qquad (26)$$

$$(B_{m,p}-1)\exp(-(B_{m,p}+1)y) -$$

$$A_{m,p}\exp(-A_{m,p}y) + B_{m,p}\exp(-B_{m,p}y)]$$

where there has been defined, $$A_{m,p} \equiv (N_{m,p}+\rho_m) \text{ and } B_{m,p} = N_{m+1,p}+1, \qquad (27)$$

and where, $\rho_m = 1-\delta_{m,1}$, is the binary function defined previously.

The derivative with respect to the OBMF amplitude is given by, $$-\frac{\partial \ln L(\vec{x})}{\partial A_{OBMF}} = -\sum_{p=1}^{N}\sum_{m=1}^{N_w(p)}\frac{(\tilde{I}_m^p - I_m^p(\vec{x}))}{\Psi_p \hat{\sigma}_{m,p}^2} \qquad (28)$$

$$F_{m,p}\left(\frac{TE_p}{T_{2,OBMF}^\dagger(p)}\right)\left(1-\exp\left(-\frac{W_p}{T_{1,OBMF}}\right)\right).$$

Derivatives for a General Dependence of Live Oil Relaxation Time and Diffusion Constant on Viscosity The derivatives of the likelihood function with respect to the crude oil constituent viscosities in Eq. (25) are valid for the particular dependence of $T_{2,o}(\eta_k)$ and $D_o(\eta_k)$ on viscosity that is given in Eqs. (5) and (10). As noted above, there is uncertainty with regard to the relaxation time and diffusion constants for live oils containing dissolved methane that can have a different dependence on viscosity than that expressed by Eqs. (5) and (10). Therefore it is useful to set forth for possible future use the general form of the derivatives with respect to the constituent viscosities, $$-\frac{\partial \ln L(\vec{x})}{\partial \eta_k} = \sum_{p=1}^{N}\sum_{m=1}^{N_w(p)}\frac{(\tilde{I}_m^p - I_m^p(\vec{x}))}{\Psi_p \hat{\sigma}_{m,p}^2} \qquad (29)$$

$$\left[\frac{b_k W_p}{T_{1,o}^2(\eta_k)}\frac{\partial T_{1,o}(\eta_k)}{\partial \eta_k}F_{m,p}\left(\frac{TE_p}{T_{2,o}^\dagger(\eta_k,p)}\right)\right.$$

$$\exp\left(-\frac{W_p}{T_{1,o}(\eta_k)}\right) + b_k F'_{m,p}\left(\frac{TE_p}{T_{2,o}^\dagger(\eta_k,p)}\right)$$

$$\left.\frac{TE_p}{(T_{2,o}^\dagger(\eta_k,p))^2}\frac{\partial T_{2,o}^\dagger(\eta_k,p)}{\partial \eta_k}\left(1-\exp\left(-\frac{W_p}{T_{1,o}}\right)\right)\right],$$

where the apparent transverse relaxation times $T_{2,o}^\dagger(\eta_k,p)$ are defined in Eq. (3).

Calculation of Parameter Covariance Matrix

The covariance matrix of the parameter estimates is useful for estimating the uncertainties in the parameter estimates. The method of calculation outlined below is identical to the method used by Freedman and Rouault (Remaining-Oil Determination Using Nuclear Magnetism Logging SPE Formation Evaluation Journal, pp. 121–130, June, 1989) The covariance or correlation matrix of the parameter estimates can be defined by, $$C_{i,j} = \langle \delta x_i \delta x_j \rangle, \qquad (30)$$

where the brackets denote a statistical or ensemble average and $\delta x_i = x_i - \langle x_i \rangle$ is the deviation of the parameter $x_i$ from its expectation value. The diagonal elements of $C_{i,j}$ are the variances in the estimated parameters. It can be shown (Stuart and Ord, Kendall's Advanced Theory Of Statistics, Oxford Univ. Press, Vol. 2, pp. 675–676, 1991) that the covariance matrix for the maximum likelihood estimates is given by the inverse of a symmetric matrix, e.g., $$C_{i,j} = M_{i,j}^{-1}, \text{ where} \qquad (31)$$

$$M_{i,j} = -\left\langle \frac{\partial^2 \ln L(\vec{x})}{\partial x_i \partial x_j}\right\rangle = \left\langle \frac{\partial \ln L(\vec{x})}{\partial x_i}\frac{\partial \ln L(\vec{x})}{\partial x_j}\right\rangle. \qquad (32)$$

Stuart and Ord (1991, supra) show that if the likelihood function obeys sufficiency and regularity conditions that are assumed to be satisfied by the functional in Eq. (15) then, $$M_{i,j} = -\left(\frac{\partial^2 \ln L(\vec{x})}{\partial x_i \partial x_j}\right)_{\vec{x}^*}, \qquad (33)$$

where the derivatives are evaluated at the maximum likelihood estimates ($\vec{x}^*$) of the parameters. The form in Eq. (33) is useful because it removes the need to compute expectation values. The elements of the matrix $M_{i,j}$ can be computed analytically.

Referring to FIG. 5 there is shown a flow diagram of a routine in accordance with an embodiment of the invention for programming one or more processors to implement a technique in accordance with the invention. In the present embodiment, the uphole processor (e.g. in equipment 7) can implement most of the routine, but the downhole processor can be involved, for example, in at least a portion of the functions of data acquisition, storage, and transmission of data to earth's surface. It will also be understood that, if desired, some of the routine can be implemented off line, such as by a remote processor at another location.

The block 521 represents selection of the suite of measurements to be made. For example, the suite of measurements may be in accordance with the types of selections indicated in the Tables of the subsequent examples. In these examples, for each of the N measurements in the suite (with p=1,2 ... N, and N=6 for these cases), there will be a different combination of $W_p$ (wait time or polarization time), $TE_p$ (echo spacing), $G_p$ (applied static magnetic field gradient), and/or $J_p$ (number of spin echoes acquired). For each measurement, p, in a measurement suite, there may be a number of repeats, it being understood that there will be a trade-off between logging speed (which is generally decreased by repeats) and noise immunity (which is generally increased by stacking data from repeats). It will also be understood that other parameters could be varied, if suitable. The block 524 represents the inputting of downhole temperature and pressure. Temperature measurement can be performed at the logging device by conventional means, either periodically or continuously, and the pressure at a given depth can be estimated from mud weight and/or local knowledge, or could be measured downhole with appropriate equipment. The suite of measurements is then implemented, as represented by the block 527.

Figure 6:
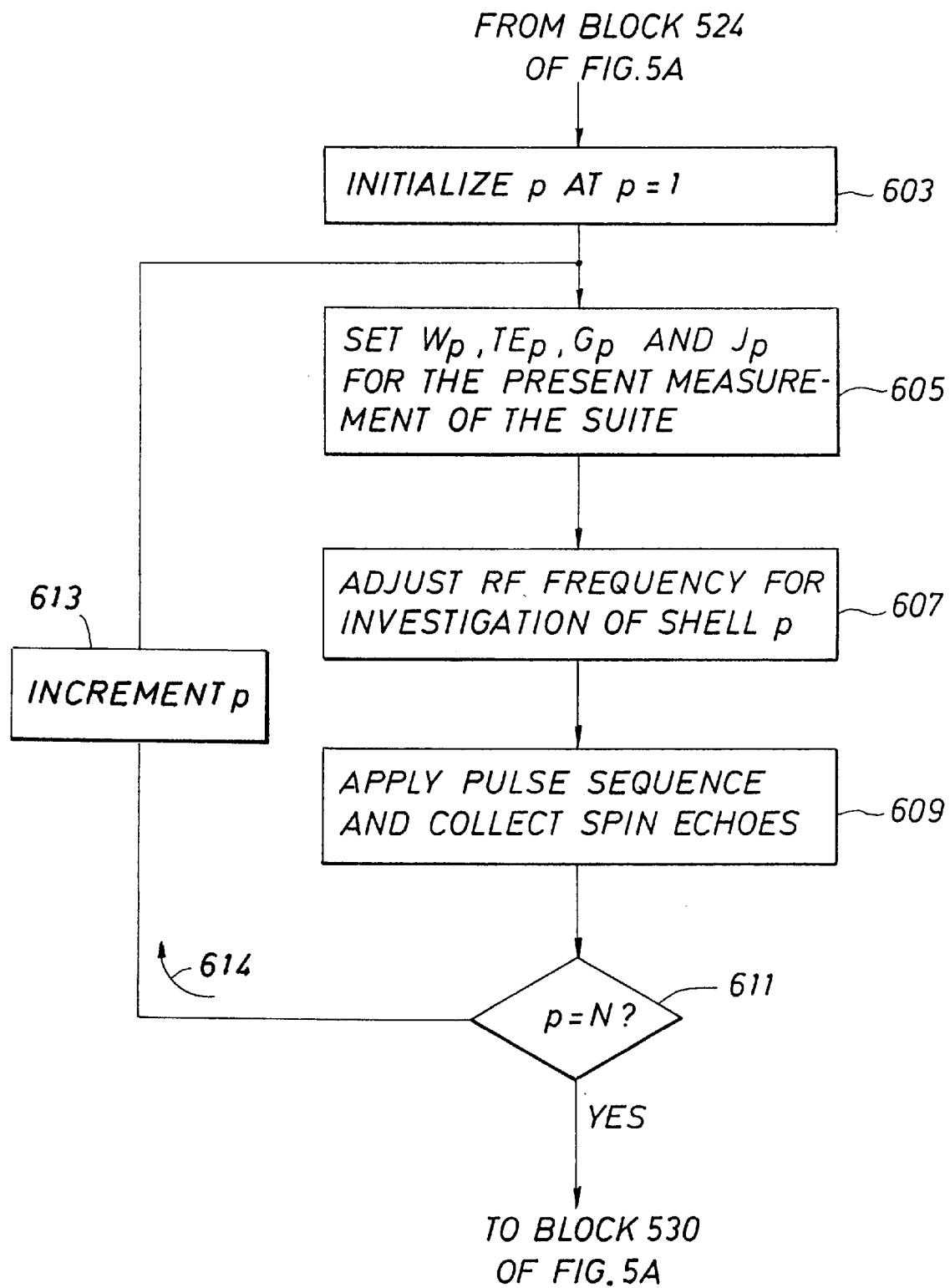
FIG. 6 is a flow diagram of a data acquisition routine that is represented by the block 527 of the FIG. 5 routine.

The block 527 represents the control of the data acquisition phase of the present embodiment, and the subroutine thereof is described in further detail in conjunction with the flow diagram of FIG. 6. Referring momentarily to FIG. 6, the index p is initialized at 1 (block 603). The measurement conditions W, TE, G, and J, are then set to $W_p$, $TE_p$, $G_p$ and $J_p$, as represented by the block 605. $W_p$ is the wait time for measurement p (wait time being the time between the end of a pulse sequence and the beginning of the next pulse sequence, during which polarization can occur), TEP is the echo spacing for the measurement p (that is, the time between successive received pulses during the pulse sequence), $G_p$ is the applied static magnetic field gradient for the measurement p, and $J_p$ is the number of spin echoes acquired for the measurement p. In the present embodiment, a CPMG pulse sequence is used, with conventional R and X receiver channels, but it will be understood that modified CPMGs or other suitable types of pulse sequences or receiver channels could be used. Then, as represented by the block 607, the RF frequency for the magnetic pulses to be employed for measurements is set at the frequency to be used for the shell p (e.g. by control of variable frequency oscillator 220 of FIG. 3). As described above, a preferred embodiment of the present invention utilizes adjacent or closely spaced thin shells of investigation region, to expedite measurements, because wait times (during which longitudinal polarization of spins in the static magnetic field is effected) can be reduced by separating the shells so that polarization in a given shell is substantially unaffected by the pulse-echo activity in another shell. Data is acquired in the closely spaced thin shells in the investigation region of the formations, the separation permitting successive acquisitions without the need for excessive wait times (for polarization), but the shells being sufficiently close together to permit an assumption that, in most cases, the formations will not vary substantially in character throughout the radial extent of the multi-shell region being investigated. (If logging time or logging speed were not a factor, the suite of measurements could all be taken in the same investigation region.) Next, as represented by the block 609, a pulse sequence is applied, for example a CPMG pulse sequence, and spin echoes are detected and stored. Inquiry is then made (decision block 611) as to whether p=N; that is, whether measurements have been taken for each shell (and thus for each set of conditions). If not, p is incremented (block 613), the block 605 is re-entered so that the conditions are set for the next p, and the loop 614 continues as the entire suite of measurements is obtained.

The diagram of FIG. 6 shows a simple case for ease of understanding. Several further considerations can come into play in selecting the shell sequences, number of repeats, and polarization wait times, given a particular desired logging speed and any time constraints it would impose. For example, although the thin shells can be relatively isolated (depending on the tool design, geometry, and shell spacing), there may be advantage to hopping, when possible, between remotely spaced shells rather than adjacent shells in order to minimize cross-talk type effects between shells. Further, it will be understood that time efficiency can be enhanced by selecting a shell hopping route that intentionally provides more wait time (for polarization or repolarization) to shells with the longer $W_p$'s. Also, as is known in the art, a "killer pulse" (e.g. an appropriately phased 90 degree pulse) can be employed, if needed, such as when hopping back to a shell for repeat of a measurement where a short wait time is called for. Thus, it will be understood that many different shell hopping routes may be suitable, depending on the circumstances.

Referring again to the flow diagram of FIG. 5, the block 530 represents the computation of the noise powers, $\psi(p)$ for the data, the computation of the regularization parameters, $\gamma(p)$, for the data, and the computation of the phase corrected data suite, $A_j(p)$. For a given measurement, it is well known that the phase corrected data can be determined by appropriate combination of the channel phases, and reference can be made to my U.S. Pat. No. 5,291,137. The noise powers $\psi(p)$ and the regularization parameters $\gamma(p)$ are useful in the inversion which, in the present embodiment, utilizes a commercially available minimization algorithm (Powell's Nonlinear Constrained Minimization Algorithm), and the window processing technique that is described in detail in my U.S. Pat. No. 5,291,137. Next, as represented by the block 534, the operator selects the type of formation model to be used; for example, a model that includes a brine phase, a crude oil phase, an oil base mud filtrate (OBMF) phase. It will be understood that the formation model can additionally or alternatively contain phases that represent, for example, gas, and also take into account internal gradients, all as described herein. The type of model selected (or initially selected, since subsequent model types can be processed) may depend on local knowledge or on other available inputs or from initial screening of the data and/or other available data. In the subsequent flow diagram description, it will be understood that treatment of a particular phase may or may not be applicable to a particular formation model being used.

The block 536 represents the specifying of constraints (including ranges, increments, and relationships) for parameters to be used in the model. As indicated above, the parameters of the model for an embodiment of the invention include (with reference to the relaxational model of equation (1)): $N_s$ amplitudes $\{a_l\}$ that define the $T_2$-distribution of the brine phase; $\xi$, the apparent $T_1/T_2$ ratio of the brine phase; the set of $N_o$ amplitudes $\{b_k\}$ that define the $T_2$-distribution of the native crude oil; the set of $N_o$ constituent viscosities $\{\eta_k\}$ of the crude oil; and $A_{OBMF}$, the amplitude of the OBMF signal. For a model that includes a gas phase, the parameters further include (with reference to equation (A.2) in Appendix A) the amplitude of the gas signal, $A_g$. For generality, the OBMF and gas terms are included subsequently in the flow diagram, although it will be understood that, depending on the circumstances, the particular model used may or may not include these components.

The block 539 represents assigning values to the constitutive relations for the crude oil; namely, constituitive relations that relate the constituent viscosities to relaxation times and diffusion constants. As described above, a value of the constituent constant a (see equations (4) and (5)) can be about 250, and the value of the constituent constant b (see equation (10a)) can be about $8.33 \times 10^{-3}$. It is understood from preceding discussions that for live oils the constitutive relations and constants will be modified according to the GOR.

The block 543 represents the computation of the brine and gas diffusion constants from known relationships using the measured temperature and estimated or measured pressure; namely $D_w(T)$ as used in equation (2) and $D_g(P,T)$ as used in equation (A.2) of Appendix A. Next, the block 546 represents the computation of gas relaxation times $T_{1,g}(P,T)$ using the measured temperature and pressure (see, for example, Kleinberg et al., 1996, supra). Then, the block 548 represents inputting the estimate of in situ viscosity of the OBMF (obtained e.g. from the drilling fluid supplier or by measurement) and the computation of the diffusion constant of the OBMF, for which equation (10) can be used.

Continuing with the description of FIG. 5, the block 550 represents the inputting of values of the hydrogen index of each of the fluids. As first noted above the hydrogen index of gas free crude oils can be estimated from the API gravity and is close to one for oils with API gravities greater than 25 (Kleinberg and Vinegar, 1996, supra). The hydrogen index of OBMF can be either measured using NMR or computed from the known chemical formula, mass density, molecular weight and number of hydrogen nuclei in the chemical formula. Formulas for the hydrogen index of live oils as a function of temperature, pressure and GOR have been published by Zhang, et al., 1998, supra. Next, as represented by the block 552, initial values are assigned to the model parameters. Then, as represented by the dashed block 560, the routine for which is described in further detail in conjunction with the flow diagram of FIG. 7, optimization of the model is implemented. As represented in simplified form in the block 560, the block 561 generally represents the determining of correspondence between signals obtained from the model and the measurement signals, and the block 562 generally represents modifying of the model. This is just a general representation, and further details of an embodiment of an optimization are set forth in conjunction with the flow diagram of FIG. 7. The optimized model parameters can then be read out, as represented by the block 570.

Figure 7:
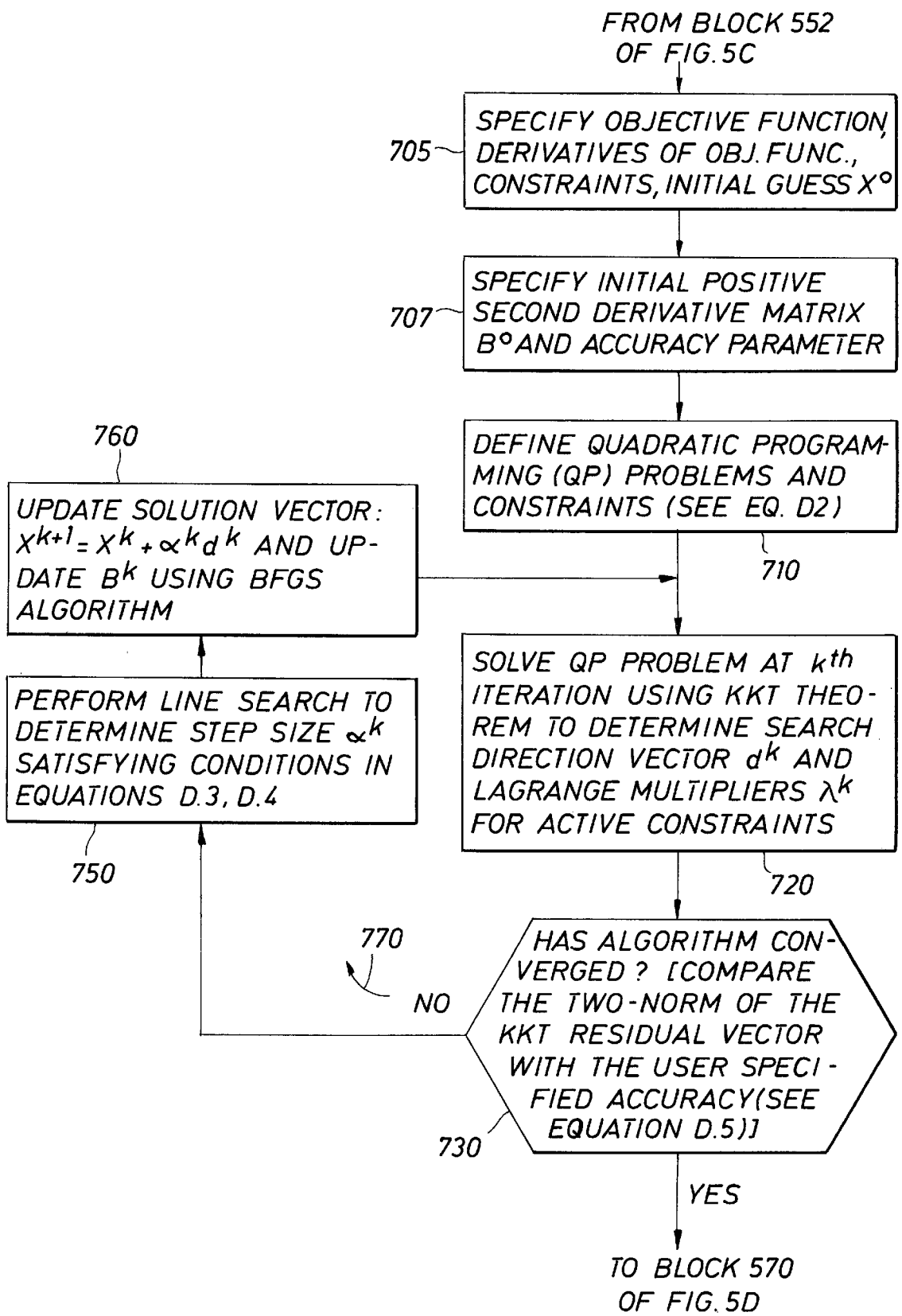
FIG. 7 is a flow diagram of a routine for model optimization as represented by the block 560 of the FIG. 5 routine.

FIG. 7 is a flow diagram of a routine for implementing Powell's Nonlinear Constrained Minimization Algorithm, which can be employed in implementing the optimization as used in an embodiment hereof. Reference can also be made to Appendix D. The block 705 represents the specifying of the objective function, derivatives of objective function, and constraints, and the selection of the initial guess $x^0$. The initial guess, if not already made (see block 552), can be specified. The initial positive definite second derivative matrix, $B^0$, and accuracy parameter are also specified (block 707). Next, as represented by the block 710, the quadratic programming (QP) problem and constraints are defined. Reference can be made to equation (D.2) of Appendix D. Next, as represented by the block 720, the quadratic programming (QP) problem is solved at the k-th iteration using the KKT Theorem to determine the search direction vector $d^k$ and Lagrange multipliers $\lambda_k$ for active constraints. Inquiry is then made (decision block 730) as to whether the algorithm has converged, such as by comparing the two-norm of the KKT residual vector with the user specified accuracy (see equation (D5) of Appendix D). If the algorithm did converge, the block 570 of FIG. 5 is entered, and the determined model parameter values can be output. If not, the blocks 750 and then 760, respectively, are entered, the block 750 representing the performing of a line search to determine step size $\alpha^k$ satisfying conditions in equations (D.3) and (D.4) of Appendix D, and the block 760 representing updating of the solution vector and updating $B^k$ using the BFGS algorithm. The block 770 is then re-entered, and the loop 770 continues until convergence is achieved.

Referring again to FIG. 5, after outputting of the optimized model parameters, the block 580 is entered, this block representing the computation of the brine-filled porosity, $\phi_w$, which can be obtained using equation (11). Also, the native oil-filled porosity, $\phi_o$, can be computed using equation (12) (block 583). Further, depending on the situation, the OBMF-filled porosity, $\phi_{OBMF}$, can be computed using equation (13) (block 585), and the gas filled porosity, $\phi_{gas}$, can be computed from equation (A.3) of Appendix A (block 587). Then, the total fluid filled porosity, A, can be computed (block 590) using equation (14) or, when gas is in the model, equation (A.4) of Appendix A. Then, using the computed fluid filled porosity, $\phi_T$, the various saturations in the investigation region (e.g. at a radius r at the center of the investigation region defined by N thin cylindrical shells) can be computed, as shown in block 592. The oil saturation, $S_o(r)$, is computed using equation (14) or (A.4), and the brine saturation, $S_w(r)$, and the OBMF saturation, $S_{OBMF}(r)$, can be computed using the relationships shown in the Figure. Further, the oil vicsosity can be computed (block 593) from the constituent viscosities using equation (8), and constants (block 594) using equations (5) and (10a) and the output model constituent viscosities. The next depth level can then be processed.

The technique hereof can also be applied to measurements taken above ground on core samples of earth formations. In such case, the core sample can be placed in MNR laboratory equipment, and an appropriate pulse sequence and echo collection can be implemented. The fluid volumes in the core and the other formation evaluation parameters provided by the technique can be determined, as described. Reference can be made to Appendix F.

Inversion Examples

The following examples may be of practical interest. The computations were done with a prototype program that implements the inversion method described hereinabove. The synthetic data were generated by a program that generates noisy spin-echo sequences using the relaxational model in Eq. (1). All of the examples in this section were computed using a pulse sequence consisting of the same six measurements. Although this sequence appears to provide good results over a wide range of fluid saturations and oil properties, it will be understood that this particular sequence or the use of six measurements is not necessarily optimum for any given situation. The examples demonstrate the efficacy of the method. Monte Carlo computations can be performed to establish the precision and accuracy of the inversion as well as to determine the best measurement sequences. The examples also show that the method hereof can be used to identify and evaluate wet zones.

Measurements and Parameters Used For Examples

The pulse parameters for the six measurements used for the examples hereof are shown in Table 1. The measurements with short wait times are needed to provide sensitivity to viscous oils with short relaxation times. The wide range of echo spacings provide maximum sensitivity to the different diffusivities of reservoir fluids and OBMF filtrates. The tool gradient may actually vary to some extent within a band of closely spaced shells, but here for convenience it is assumed to be a constant. Note from Eqs. (2), (3) and (9) that it is the product of the tool gradient and the echo spacing that affects apparent relaxation times. Thus any errors in the tool gradient assumed in the inversion are equivalent to a change in echo spacings as far as the diffusion effects are concerned. In particular, in formations with internal gradients assuming an incorrect gradient for the inversion will not necessarily degrade the inversion depending on the robustness of the measurement sequence to changes in echo spacing and the magnitude of the gradient errors.

TABLE 1

Measurement Parameters

| Measurement | TE (ms) | W (s) | G (Gauss/cm) | J | Repeats |
|---|---|---|---|---|---|
| 1 | 0.2 | 6.0 | 25 | 3000 | 5 |
| 2 | 0.3 | 1.0 | 25 | 600 | 5 |
| 3 | 0.6 | 0.15 | 25 | 200 | 50 |
| 4 | 1.0 | 0.08 | 25 | 100 | 50 |
| 5 | 2.0 | 0.05 | 25 | 100 | 50 |
| 6 | 4.0 | 0.02 | 25 | 30 | 50 |

A formation temperature of 100 degrees Centigrade is used for all the computations. The diffusion constant for the brine phase at formation temperature is commputed using a polynomial fit to the published data for water diffusion constant versus temperature. The equation for $D_w(T)$ that was used for the computations is, $$D_w(T)=35\times10^{-9}(T-273.16)^2+3.62\times10^{-7}(T-273.16)+1.17\times10^{-5}(cm^2/s), \quad (34)$$

where T is the formation temperature in degrees Kelvin. For the inversion examples hereof, the formation temperature was assumed to be 100 degrees Centigrade so that the brine diffusion constant computed from the above equation is $8.29\times10^{-5} cm^2/s$.

Figure 8:
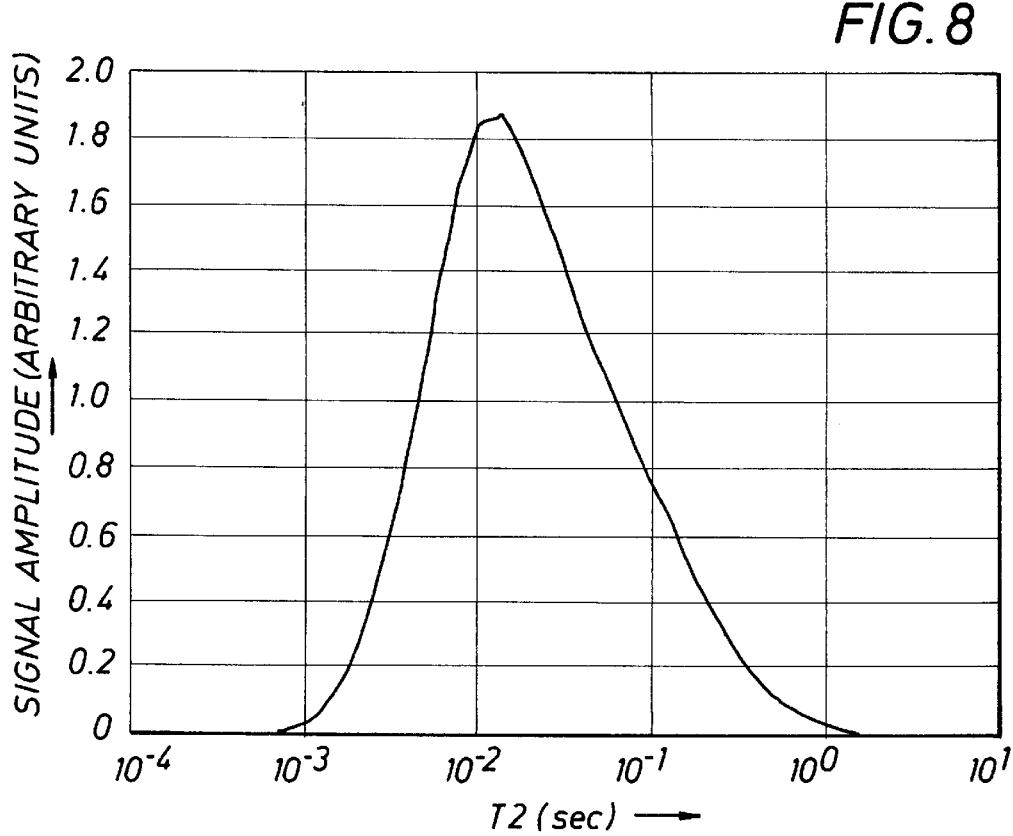
FIG. 8 is a plot of a brine $T_2$ distribution in a sandstone formation, as used in an inversion example hereof.

The brine $T_2$ -distribution that was used for all of the computations in the examples was selected from (e.g., at one particular depth) the suite of 30 distributions that have been used previously (e.g. in the above-referenced U.S. patent application Ser. No. 09/156,417 for Monte Carlo simulations. This brine $T_2$-distribution is shown in FIG. 8.

The synthetic spin echo date are generated using OBMF bulk spin relaxation times, $T_{1,OBMF}=T_{2,OBMF}=3$ s and OBMF viscosity, $\eta_{OBMF}=2$ cp. Also in generating the synthetic data, the constituent constants used in equations in Eqs. (4), (5) and (10) were those given by Looyestijn (1996, supra), e.g., a=250 and b=8.33×10$^{-3}$. For convenience and without loss of generality, the hydrogen indexes of the brine, crude oil and OBMF liquids are assumed to be equal to one for all the examples.

In all computations, the number of brine spectral components $N_w=41$, and the number of crude oil spectral components, $N_o=8$. The total number of unknown parameters was therefore equal to 59 in all computations (except for the gas examples in Appendix A for which there are 60 unknown parameters).

EXAMPLE NO. 1
Brine Filled Formation

The first example is for a formation filled 100% with brine. The formation input parameters and results of and inversion are shown in Table 2. The "carets" over the parameters are used to indicate that these are the estimates from the inversion. The first set of estimates were obtained by inverting the synthetic spin-echo data assuming the same OBMF properties and the constituent equation constants used to generate the spin-echoes. In practice there will be errors in the OBMF properties and constituent constants assumed by the inversion. In order to get a feel for the effect of such errors, the inversions were repeated assuming OBMF properties and constituent equation constants that are different from those used to generate the spin echo data. The assumed OBMF properties for the repeated inversions were $T_{1,OBMF}=T_{2,OBMF}=2$ s and $\eta_{OBMF}=1$ cp which differ by 50% from the values used to generate the spin echoes. The constants assumed for the repeated inversions differed by 20% from their input values , e.g., the values assumed in the repeated inversions were a=300 and b=1.0×10$^{-2}$. The results of the repeated inversions are shown by the numbers in parenthesis in the tables.

TABLE 2

100% Brine Filled Formation
Inputs:
$\phi_o = \phi_{OBMF} = 0, \phi_w = \phi_T = 20$ p.u., $S_o = 0, \xi = 1.5$

| Noise Per Echo | $\sqrt{\Psi} = 2.0$ p.u. | $\sqrt{\Psi} = 4.0$ p.u. |
|---|---|---|
| $\hat{\xi}$ | 1.55 (1.56) | 1.43 (1.43) |
| $\hat{S}_o$ | 5.1E-4 (4.5E-3) | 5.0E-4 (5.0E-4) |
| $\hat{\phi}_T$ | 19.5 (19.5) | 19.9 (19.9) |
| $\hat{\phi}_o$ | 1.0E-2 (9.0E-2) | 1.0E-2 (1.0E-2) |
| $\hat{\phi}_w$ | 19.5 (19.4) | 19.9 (19.9) |
| $\hat{\phi}_{OBMF}$ | 1.3E-5 (1.3E-5) | 1.3E-5 (1.3E-5) |

Note that the inversion of the data is robust and, in particular, no oil is predicted and no changes in the parameter estimates were produced by assuming incorrect values for the OBMF properties and the constitutive constants in Eqs. (4), (5) and (10).

EXAMPLE NO.2
Brine and OBMF Filled Formation

The input formation parameters and the results of the inversion are shown in Table 3. Note the inversion of the noisy data is robust and that only non-commercial quantities (i.e., oil saturations of 1.5% and 4.7%) of crude oil are predicted for a noise per echo of 2.0 p.u. For the higher noise level of 4.0 p.u. per echo the predicted oil saturations (e.g., 4.7% and 9.6%) increase but are not commercially significant. That is, the formation is predicted to be more than 90% brine saturated and would in formation evaluation correctly be considered to be a "wet" zone. Note that total fluid filled porosity and brine filled porosity are correctly predicted. Note that the predicted crude oil is due to under estimation of OBMF and brine filled porosity.

TABLE 3

Brine and OBMF Filled Formation
Inputs:
$\phi_o = 0, \phi_{OBMF} = 10$ p.u., $\phi_w = 10$ p.u., $\phi_T = 20$ p,u., $S_o = 0, \xi = 1.5$

| Noise Per Echo | $\sqrt{\Psi} = 2.0$ p.u. | $\sqrt{\Psi} = 4.0$ p.u. |
|---|---|---|
| $\hat{\xi}$ | 1.4 (1.6) | 1.6 (2.1) |
| $\hat{S}_o$ | 1.50E-2 (4.7E-2) | 4.7E-2 (9.6E-2) |
| $\hat{\phi}_T$ | 19.9 (19.5) | 19.1 (18.8) |
| $\hat{\phi}_o$ | 0.3 (0.92) | 0.9 (1.8) |
| $\hat{\phi}_w$ | 10.4 (10.6) | 8.7 (8.2) |
| $\hat{\phi}_{OBMF}$ | 9.2 (8.0) | 9.5 (8.9) |

EXAMPLE NO.3
Brine, OBMF and Oil Filled Formation

This example is for a formation that contains brine, native oil and OBMF. This inversion is done for a low viscosity oil ($\eta_0$=5.7 cp), a high viscosity oil ($\eta_0$=71.7 cp) and a "[1]very low viscosity oil" ($\eta_0$=1.65 cp ). For the purposes hereof, a very low viscosity oil is one with a viscosity comparable to that assumed for the OBMF (i.e., 1.0 and 2.0 cp). The formation input parameters and results of the inversion for the low viscosity oil are shown in Table 4.

TABLE 4

Brine, Oil and OBMF Filled Formation
Low Viscosity Oil
Inputs:
$\phi_o$ = 10 p.u., $\phi_{OBMF}$ = 10 p.u., $\phi_w$ = 10 p.u., $\phi_T$ = 30 p.u.,
$S_o$ = 0.33, $\eta_o$ = 5.7, $\xi$ = 1.5
Constituent Viscosities: 20., 10., 5., 3.

| Noise Per Echo | $\sqrt{\Psi}$ = 2.0 p.u. | $\sqrt{\Psi}$ = 4.0 p.u. |
|---|---|---|
| $\hat{\xi}$ | 1.3 (1.65) | 2.5 (3.2) |
| $\hat{S}_o$ | 0.31 (0.32) | 0.37 (0.36) |
| $\hat{\phi}_T$ | 29.6 (28.8) | 29.9 (29.1) |
| $\hat{\phi}_o$ | 9.3 (9.2) | 11.2 (10.5) |
| $\hat{\phi}_w$ | 10.1 (8.3) | 8.3 (7.4) |
| $\hat{\phi}_{OBMF}$ | 10.2 (11.3) | 10.4 (11.3) |
| $\hat{\eta}_o$ | 6.5 (6.5) | 6.4 (7.1) |

Note the good identification of all three fluids for both 2 and 4 p.u. of noise per echo and also that the bulk oil viscosity was computed accurately for a broad distribution of constituent viscosities. Also, note that relatively minor changes (e.g., the numbers in parenthesis) in the parameter estimates were caused by assuming incorrect OBMF properties and constitutive constants in the inversion.

Table 4a contains the inputs and the inversion results for a high viscosity oil. Note that all the other inputs except for viscosities are identical to those in Table 4.

TABLE 4a

Brine, Oil and OBMF Filled Formation
High Viscosity Oil
Inputs:
$\phi_o$ = 10 p.u., $\phi_{OBMF}$ = 10 p.u., $\phi_w$ = 10 p.u., $\phi_T$ = 30 p.u.,
$S_o$ = 0.33, $\eta_o$ = 71.7, $\xi$ = 1.5
Constituent Viscosities: 100., 70., 80., 50.

| Noise Per Echo | $\sqrt{\Psi}$ = 2.0 p.u. | $\sqrt{\Psi}$ = 4.0 p.u. |
|---|---|---|
| $\hat{\xi}$ | 1.4 (1.1) | 1.2 (1.6) |
| $\hat{S}_o$ | 0.31 (0.30) | 0.13 (0.34) |
| $\hat{\phi}_T$ | 29.6 (28.9) | 29.5 (29.4) |
| $\hat{\phi}_o$ | 9.1 (8.7) | 3.7 (10.0) |
| $\hat{\phi}_w$ | 10.5 (14.2) | 16.3 (12.7) |
| $\hat{\phi}_{OBMF}$ | 10.0 (5.96) | 9.4 (6.7) |
| $\hat{\eta}_o$ | 72.4 (11.2) | 53.7 (19.3) |

Note that accurate fluid saturations are obtained for 2.0 p.u. of noise. The numbers in parenthesis show that for 2 p.u. and 4.0 p.u. of noise the oil reservoir is still identified even if there are errors in the assumed OBMF properties and in the constitutive equations. The latter errors cause the oil viscosity to be underestimated and the volumes of brine and OBMF to be over and underestimated, respectively.

The water saturation is considerably overestimated and the oil saturation underestimated for the data with 4.0 p.u. of noise. Observe that the total fluid filled porosity is accurately recovered with 4 p.u. of noise. This result indicates that data with high SNR are probably required to determine accurate saturations in reservoirs with high viscosity oils (i.e., short relaxation times). The inversion would fail completely for extreme cases (e.g., $\eta_o$=1000 cp) for which the bulk relaxation times are of the order of 1.5 ms.

Table 4b contains the inputs and the inversion results for a very low viscosity oil. Note that all the other inputs except for viscosities are identical to those in Tables 4 and 4a.

TABLE 4b

Brine, Oil and OBMF Filled Formation
Very Low Viscosity Oil
Inputs:
$\phi_o$ = 10 p.u., $\phi_{OBMF}$ = 10 p.u., $\phi_w$ = 10 p.u., $\phi_T$ = 30 p.u.,
$S_o$ = 0.33, $\eta_o$ = 1.65, $\xi$ = 1.5
Constituent Viscosities: 5., 3., 1., 0.5

| Noise Per Echo | $\sqrt{\Psi}$ = 2.0 p.u. | $\sqrt{\Psi}$ = 4.0 p.u. |
|---|---|---|
| $\hat{\xi}$ | 1.4 (1.6) | 1.2 (1.2) |
| $\hat{S}_o$ | 0.16 (0.13) | 0.11 (0.08) |
| $\hat{\phi}_T$ | 31.3 (30.1) | 32.0 (31.0) |
| $\hat{\phi}_o$ | 5.0 (3.8) | 3.6 (2.5) |
| $\hat{\phi}_w$ | 12.1 (10.3) | 14.6 (12.3) |
| $\hat{\phi}_{OBMF}$ | 14.21 (16.0) | 13.8 (16.2) |
| $\hat{\eta}_o$ | 3.5 (4.6) | 2.6 (3.8) |

The very low viscosity oil makes it very difficult to accurately separate the brine, oil and OBMF because the viscosity contrasts are small. It is not a SNR issue but rather a question of the various fluids having very similar responses to the measurements. Note that the inversion confuses native oil with both brine and OBMF. It is a fundamental problem of lack of contrast in fluid properties and one cannot expect to alter this circumstance by either improved SNR or by choosing a different suite of measurements.

EXAMPLE NO 4

Brine and Oil Filled Formation

The last of this group of examples is a brine and oil filled formation containing no OBMF at the DOI of the measurements. Table 5 contains the inputs and inversion results for a low viscosity oil.

TABLE 5

Brine and Oil Filled Formation
Low Viscosity Oil
Inputs:
$\phi_o$ = 20 p.u., $\phi_{OBMF}$ = 0 p.u., $\phi_w$ = 10 p.u., $\phi_T$ = 30 p.u.,
$S_o$ = 0.67, $\eta_o$ = 5.7, $\xi$ = 1.5
Constituent Viscosities: 20., 10., 5., 3.

| Noise Per Echo | $\sqrt{\Psi}$ = 2.0 p.u. | $\sqrt{\Psi}$ = 4.0 p.u. |
|---|---|---|
| $\hat{\xi}$ | 1.13 (1.24) | 1.05 (1.07) |
| $\hat{S}_o$ | 0.60 (0.64) | 0.54 (0.56) |
| $\hat{\phi}_T$ | 29.7 (29.7) | 29.3 (29.3) |
| $\hat{\phi}_o$ | 17.9 (19.0) | 15.8 (16.3) |
| $\hat{\phi}_w$ | 11.8 (10.4) | 13.5 (13.0) |
| $\hat{\phi}_{OBMF}$ | 1.25E−5 (0.26) | 1.25E−5 (1.25E−5) |
| $\hat{\eta}_o$ | 6.4 (5.3) | 7.2 (6.2) |

The inversion recovers accurately the true OBMF filled porosity and the total fluid filled porosity. Although, the oil filled porosity is slightly underestimated, the results for the oil saturation, oil viscosity and total fluid filled porosity are excellent. Note that there are relatively minor changes in the estimates in parenthesis, e.g., when the inversion uses incorrect values for the OBMF properties and the constants in the constitutive equations.

Table 5a contains the inputs and the inversion results for a high viscosity oil. Note that all the other inputs except for viscosities are identical to those in Table 5.

TABLE 5a

Brine and Oil Filled Formation
High Viscosity Oil
Inputs:
$\phi_o = 20$ p.u., $\phi_{OBMF} = 0$ p.u., $\phi_w = 10$ p.u., $\phi_T = 30$ p.u.,
$S_o = 0.67$, $\eta_o = 71.7$, $\xi = 1.5$
Constituent Viscosities: 100., 70., 80., 50.

| Noise Per Echo | $\sqrt{\Psi} = 2.0$ p.u. | $\sqrt{\Psi} = 4.0$ p.u. |
|---|---|---|
| $\hat{\xi}$ | 1.5 (1.5) | 1.3 (1.3) |
| $\hat{S}_o$ | 0.55 (0.55) | 0.56 (0.56) |
| $\hat{\phi}_T$ | 30.1 (30.1) | 29.9 (29.9) |
| $\hat{\phi}_o$ | 16.7 (16.7) | 16.7 (16.8) |
| $\hat{\phi}_w$ | 13.4 (13.4) | 13.2 (13.1) |
| $\hat{\phi}_{OBMF}$ | 6.33E–2 (6.5E–2) | 1.25E–5 (1.25E–5) |
| $\hat{\eta}_o$ | 66.4 (55.3) | 66.6 (55.3) |

The results in Table 5a for a high viscosity oil in a brine and oil filled formation are very good. The results for the two noise levels are surprisingly close. The oil saturations from the inversion are more accurate than those that can be expected from computations based on saturation equations (e.g., Archie or Dual-Water) and electrical log measurements. Note that there are essentially no changes in the estimates in parenthesis, e.g., when the inversion uses incorrect values for the OBMF properties and the constants in the constitutive equations.

Table 5b contains the inputs and the inversion results for a very low viscosity oil. Note that all the other inputs except for viscosities are identical to those in Tables 5 and 5a.

TABLE 5b

Brine and Oil Filled Formation
Very Low Viscosity Oil
Inputs:
$\phi_o = 20$ p.u., $\phi_{OBMF} = 0$ p.u., $\phi_w = 10$ p.u., $\phi_T = 30$ p.u.,
$S_o = 0.67$, $\eta_o = 1.65$, $\xi = 1.5$
Constituent Viscosities: 5., 3., 1., 0.5

| Noise Per Echo | $\sqrt{\Psi} = 2.0$ p.u. | $\sqrt{\Psi} = 4.0$ p.u. |
|---|---|---|
| $\hat{\xi}$ | 1.2 (1.3) | 1.2 (1.2) |
| $\hat{S}_o$ | 0.30 (0.31) | 0.23 (0.22) |
| $\hat{\phi}_T$ | 30.9 (30.2) | 32.9 (32.2) |
| $\hat{\phi}_o$ | 9.2 (9.3) | 7.6 (7.2) |
| $\hat{\phi}_w$ | 13.3 (11.2) | 16.9 (15.0) |
| $\hat{\phi}_{OBMF}$ | 8.4 (9.7) | 8.4 (10.1) |
| $\hat{\eta}_o$ | 3.8 (3.9) | 4.2 (4.0) |

The inversion confuses the low viscosity oil with the OBMF and brine as was the case shown in Table 4b of Example No. 3 discussed previously. Nevertheless, an oil reservoir would be identified by the inversion albeit with pessimistic oil saturations because of the very low viscosity oil.

Monte Carlo Results for Hydrocarbon Identification in a Carbonate Formation

Figure 9:
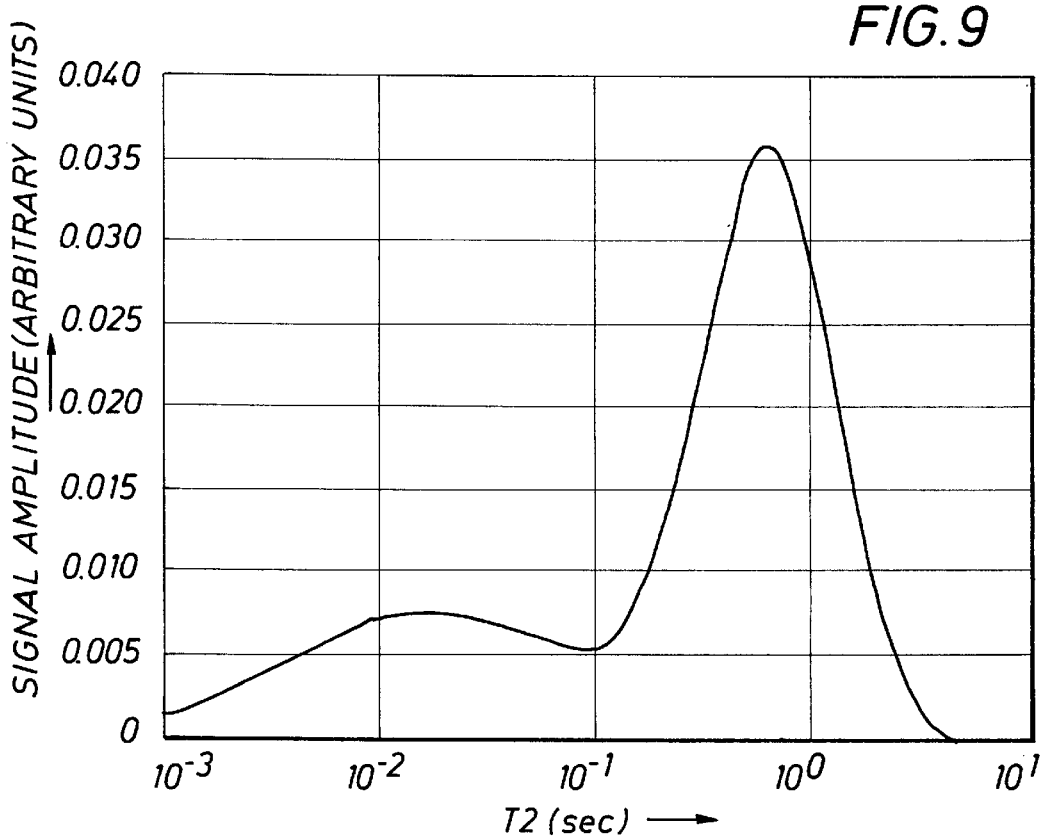
FIG. 9 is a plot of a brine $T_2$-distribution in a carbonate formation, as used in another inversion example hereof.

This example presents the results of Monte Carlo simulations for a model carbonate formation that contains oil, gas, OBMF and brine. The brine $T_2$-distribution used to generate synthetic spin-echoes for the simulations is shown in FIG. 9. The measurement suite for the carbonate Monte Carlo simulation consisted of the six measurements shown in Table 6. Note that the short wait times in the suite have been increased compared to those in Table 1. The reason is the difference in the character of the $T_2$-distributions. The distribution in FIG. 8 has most of its amplitude associated with relaxation times below 100 ms whereas the distribution in FIG. 9 has very little amplitude in this range. The carbonate simulation was performed using the $T_2$-distribution in FIG. 9 to generate 25 noise free spin-echo sequences. Additive random noise with 4.0 p.u. standard deviation per echo per measurement was added to each CPMG sequence in the suite after first reducing the noise by the square root of the number of repeats shown in Table 1. The CPMG's for the Monte Carlo sequence were generated using a constant value of $T_1/T_2=1.8$.

TABLE 6

Measurement Parameters for Carbonate Monte Carlo Simulation

| Measurement | TE (ms) | W (s) | G (Gauss/cm) | J | Repeats |
|---|---|---|---|---|---|
| 1 | 0.2 | 6.0 | 25 | 3000 | 5 |
| 2 | 0.3 | 1.0 | 25 | 600 | 5 |
| 3 | 0.6 | 0.45 | 25 | 200 | 50 |
| 4 | 1.0 | 0.3 | 25 | 100 | 50 |
| 5 | 2.0 | 0.15 | 25 | 100 | 50 |
| 6 | 4.0 | 0.1 | 25 | 30 | 50 |

Figure 10:
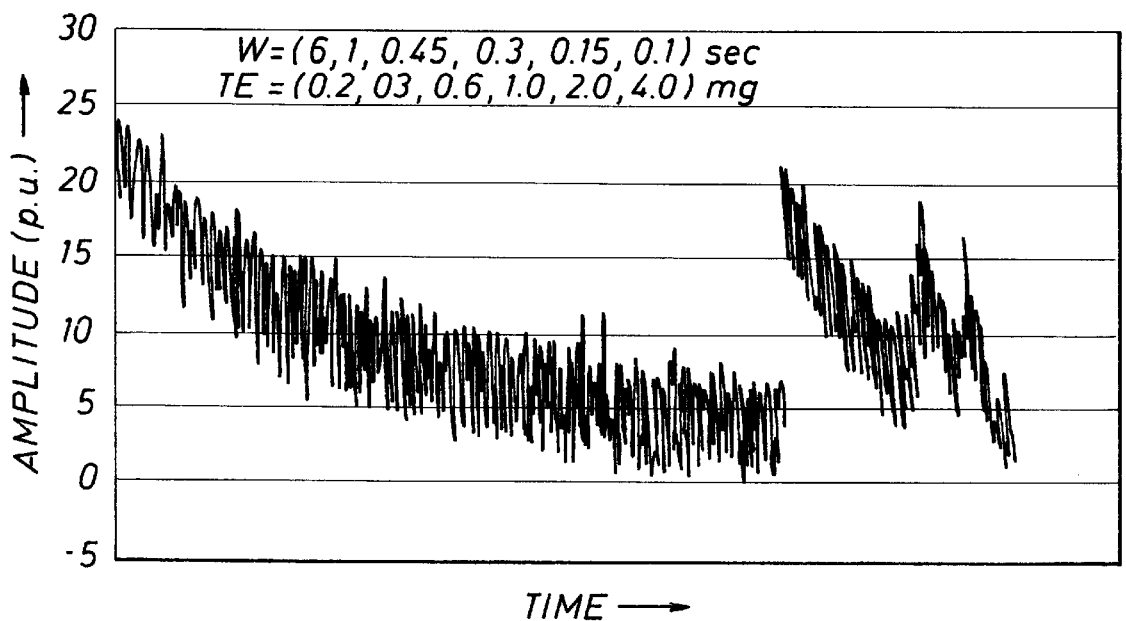
FIG. 10 is a graph of echo amplitude as a function of time for a measurement suite used in an inversion example.
Figure 11:
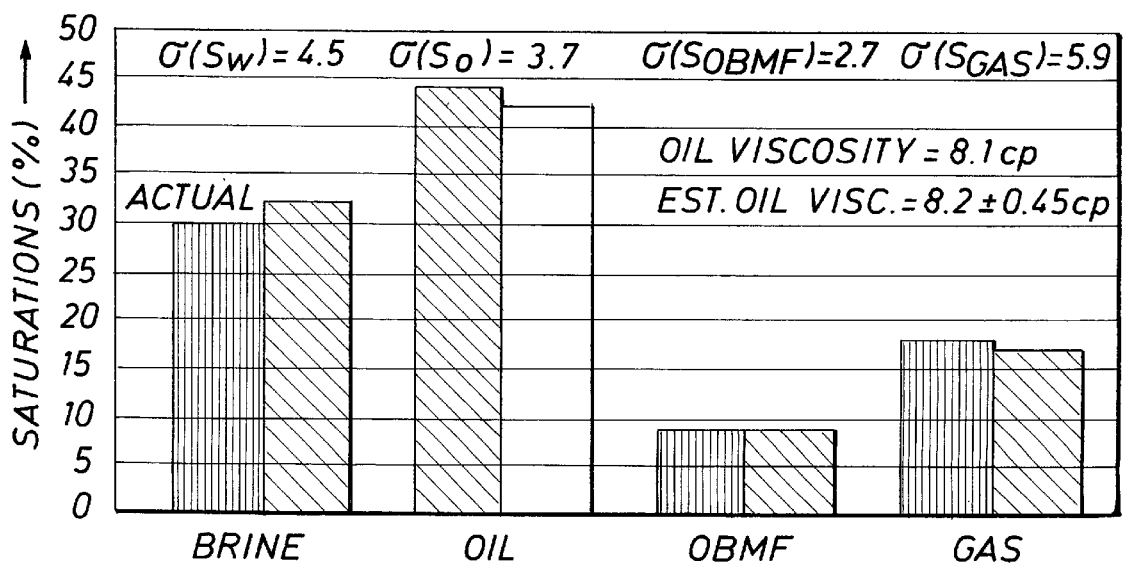
FIG. 11 is a bar graph, for brine, oil, OBMF, and gas, comparing true (input) saturations with those obtained from a technique in accordance with an embodiment of the invention in a Monte Carlo simulation using the FIG. 10 measurements.

FIG. 10 shows the measurement suite. FIG. 11 is a plot of the input (i.e., actual) fluid saturations and the mean estimated saturations from the Monte Carlo simulation using the inversion model hereof. The standard deviations in the computed saturations are also shown. Also the true oil viscosity, the estimated viscosity, and its standard deviation are shown.

Tool Motion Effects

Figure 12:
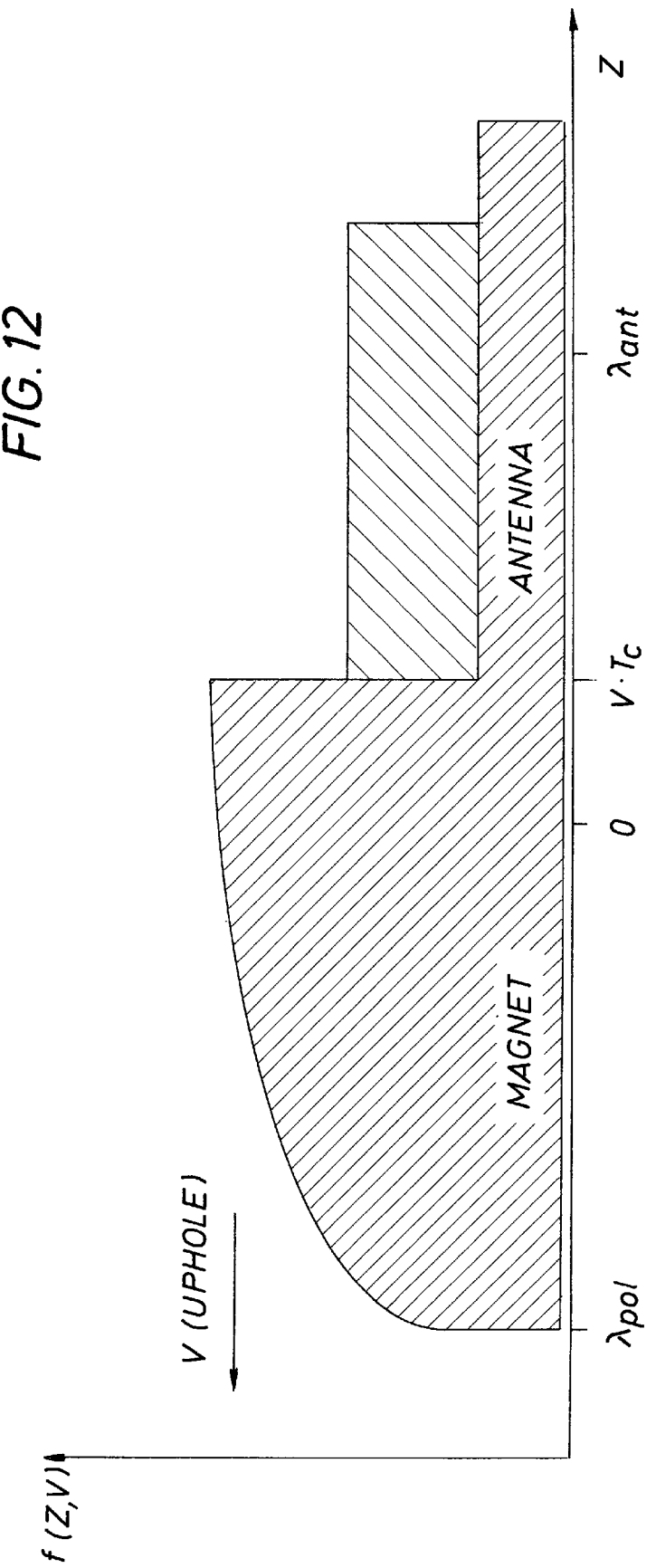
FIG. 12 is a diagram showing a polarization profile produced in a formation by a moving logging device having a pre-polarization section and which can be used to obtain measurements that are compensated for logging device velocity in accordance with an embodiment of the invention.
Figure 13:
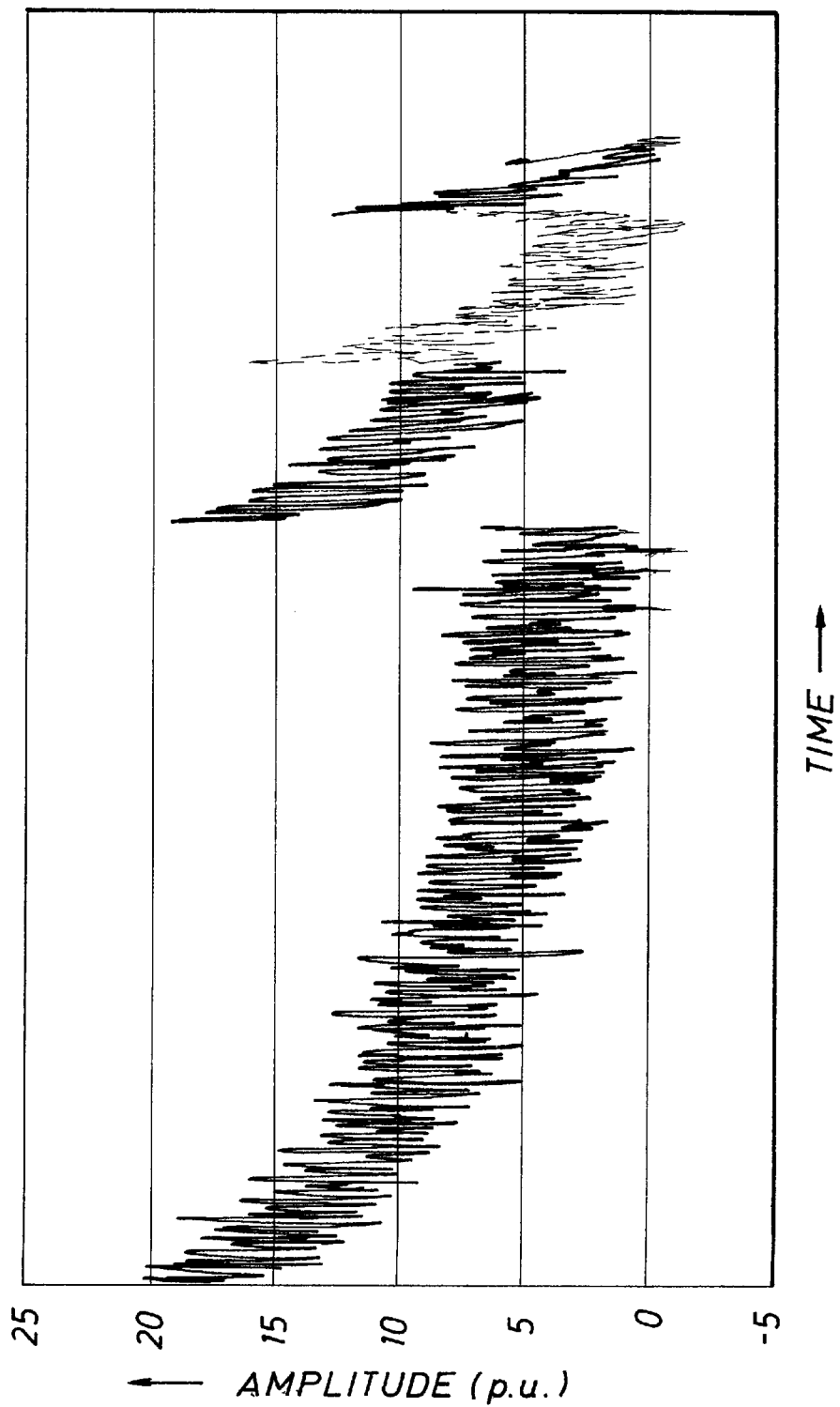
FIG. 13 is a graph of echo amplitude as a function of time for a measurement suite used in another inversion example.
Figure 14:
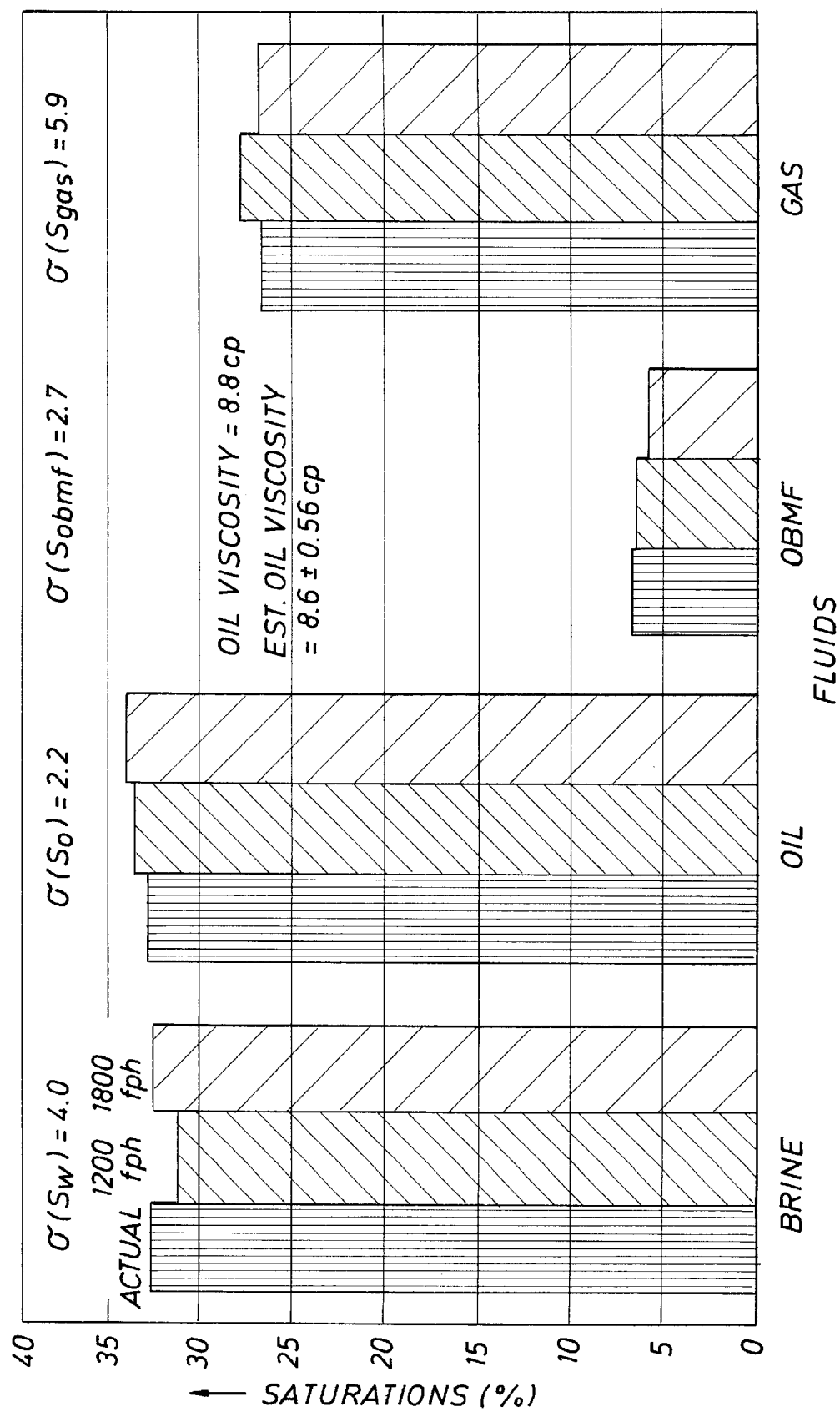
FIG. 14 is a bar graph, for brine, oil, OBMF, and gas, comparing true (input) saturations with those obtained from a technique in accordance with an embodiment of the invention in a Monte Carlo simulation using the FIG. 13 measurements.

To this point, the effects of tool motion are not included in the relaxation models. The polarization functions in Eqs. (1) and (A.1) that describe the approach of the longitudinal magnetization towards its equilibrium value are valid for a stationary tool. In this section hereof a speed dependent polarization function for constant tool speed is derived. This function properly accounts for the fact that the formation polarization varies along the length of the tool. The polarization profile f(z, v) is shown in FIG. 12 for a logging tool moving uphole at constant speed (v). The tool has an antenna of length $i_{ant}$ and a magnet with a pre-polarization length $I_{pol}$. The z-axis is part of a reference frame fixed in the formation and is parallel to the axis of the borehole. The cycle time $T_c$ is defined as the total time for a measurement, i.e., the sum of the echo acquisition time and the wait time. The wait time is the dead time, after echo acquisition is over, before a ninety-degree (or more generally a$\alpha$-degree) pulse is initiated to start the next measurement cycle. The FIG. 12 depicts a snapshot of the tool at the instant before a new measurement cycle is initated by application of a ninety degree pulse. During the previous measurement the tool moved a distance $vT_c$. Note that the polarization profile opposite the antenna is discontinuous. The first part has been polarized by the pre-polarization magnet located ahead of the antenna. The second part is polarized during the dead time following echo acquisition. See U.S. Pat. No. 5,055, 788.

The measurement depicted in FIG. 12 is an "overlapping" measurement because the distance the tool moves during the measurement cycle time is less than the antenna length. If the tool moves a distance equal to the antenna length during a measurement cycle time then the measurement is called "non-overlapping." A general suite of measurements acquired for hydrocarbon detection will necessarily consist of both overlapping and non-overlapping measurements. The non-overlapping measurements involve partial polarization of the fluids in the formation and provide the measurement suite with sensitivity to the different $T_1$ relaxation times of the formation fluids. In FIG. 12 one can see that the details of the polarization profile in the formation depend on the logging speed. Therefore failure to account for logging speed effects can lead to erroneous results. Non-overlapping measurements provide full polarization and allow fast logging by taking advantage of the magnet pre-polarization length. The speed dependent polarization functions derived below are valid for both types of measurements.

Speed Dependent Polarization Functions

Let f(z, v) denote the speed-dependent polarization profile. The polarization profile is defined by, $$f(z, v) = 1 - \exp\left(-\frac{T(z, v)}{T_1}\right), \tag{35}$$

where T(z, v) is the recovery time for spins in the formation located at position z opposite the antenna (see FIG. 12) and $T_1$ is the longitudinal relaxation time of the formation. The form of Eq. (35) is valid provided that the magnitude of static magnetic field in the pre-polarization region is effectively the same as the field opposite the antenna (i.e., there are no non-equilibrium transient effects in the longitudinal magnetization). The cycle time for the measurement is by definition, $$T_c = W + J*TE, \tag{36}$$

where w is the wait time, j the total number of echoes and TE the echo spacing. The polarization time varies along the length of the antenna and in the overlap region is constant and given by;

$$T(z,v) = W, \text{ for } vT_c \leq z \leq l_{ant}, \tag{37a}$$

whereas in the non-overlap region of the measurement, $$T(z, v) = \frac{l_{pol} + z}{v}, \text{ for } 0 \leq z \leq vT_c. \tag{37b}$$

The speed dependent polarization function f(v) is obtained by multiplying f(z,v) by the antenna sensitivity function $S_a(z)$ and integrating over the antenna, i.e., $$f(v) = \int_0^{l_{ant}} dz S_a(z) f(z, v) = \int_0^{l_{ant}} dz \frac{f(z, v)}{l_{ant}}, \tag{38}$$

where in obtaining the last equality we have assumed that the sensitivity of the antenna is uniform along its length. Using Eqs. (35) and (37) one finds on performing the integration, $$f(v) = \frac{vT_c}{l_{ant}} - \frac{vT_1}{l_{ant}}\left(1 - \exp\left(-\frac{T_c}{T_1}\right)\right)\exp\left(-\frac{l_{pol}}{vT_1}\right) + \tag{39}$$

$$\left(1 - \exp\left(-\frac{W}{T_1}\right)\right)\frac{(l_{ant} - vT_c)}{l_{ant}},$$

function in Eq. (39) reduces to the form used in Eq. (1) for a stationary measurement. Also, observe that for a non-overlapping measurement, i.e., if $vT_c = l_{ant}$, the third term vanishes. To incorporate speed effects into the relaxational models, the polarization functions in Eqs. (1) and (A. 1) are replaced by f(v) which is valid for both overlapping and non-overlapping measurements. Parts of the formation will be missed by the measurements if $vT_c > l_{ant}$.

Analytical Derivatives for the Inversion with Speed Corrections

The minimization of the objective functional in Eq. (15) including speed dependent polarization functions can be performed following the same procedure as discussed for a stationary tool. The minimization is made more robust and computationally cheaper by the use of analytically derived derivatives. The analytical forms of most of the derivatives derived earlier for a stationary tool are still valid. For example the derivatives in Eqs. (21), (24) and (28) are correct for a moving tool if one simply replaces the stationary polarization functions by the speed dependent polarization function. The derivatives in Eqs. (22) and (25) with respect to apparent brine $T_1/T_2$ ratio ($\xi$) and crude oil constituent viscosities ($\eta_k$), however, are modified because of the more complex $T_1$ dependence of the speed dependent polarization function. The derivative with respect to 4 for a moving tool is given by, $$-\frac{\partial \ln L(\vec{x})}{\partial \xi} = \xi^{-2} \sum_{p=1}^{N} W_p \left(\frac{l_{ant} - vT_c^p}{l_{ant}}\right) \sum_{m=1}^{N_w(p)} \frac{(\tilde{I}_m^p - I_m^p(\vec{x}))}{\Psi_p \hat{\sigma}_m^2} \tag{40}$$

$$S_{m,p}^{(1)}(\xi) + -\frac{v}{\xi l_{ant}} \sum_{p=1}^{N} T_c^p \sum_{m=1}^{N_w(p)} \frac{(\tilde{I}_m^p - I_m^p(\vec{x}))}{\Psi_p \hat{\sigma}_m^2}$$

$$S_{m,p}^{(2)}(\xi, v) + \sum_{p=1}^{N} \sum_{m=1}^{N_w(p)} \frac{(\tilde{I}_m^p - I_m^p(\vec{x}))}{\Psi_p \hat{\sigma}_m^2} S_{m,p}^{(3)}(\xi, v),$$

where $T_c^p = W^p + j_p TE_p$ is the cycle time for measurement p. The first term in Eq. (40) accounts for the overlapping part of the measurement. Note that it vanishes for non-overlapping measurements, i.e., when $vT_c^p = l_{ant}$. In Eq. (40) the following summations have been defined, $$S_{m,p}^{(1)}(\xi) = \sum_{l=1}^{N_s} \frac{a_l}{T_{2,l}} F_{m,p}\left(\frac{TE_p}{T_{2,l}^\dagger(p)}\right) \exp\left(-\frac{W_p}{\xi T_{2,l}}\right), \tag{40a}$$

$$S_{m,p}^{(2)}(\xi, v) = \sum_{l=1}^{N_s} a_l F_{m,p}\left(\frac{TE_p}{T_{2,l}^\dagger(p)}\right) \exp\left(-\frac{l_{pol}}{v\xi T_{2,l}}\right) \exp\left(-\frac{T_c^p}{\xi T_{2,l}}\right), \tag{40b}$$

$$S_{m,p}^{(3)}(\xi, v) = \sum_{l=1}^{N_s} a_l F_{m,p}\left(\frac{TE_p}{T_{2,l}^\dagger(p)}\right) \tag{40c}$$

$$\left(\frac{vT_{2,l}}{l_{ant}} + \frac{l_{pol}}{\xi l_{ant}}\right) \exp\left(-\frac{l_{pol}}{v\xi T_{2,l}}\right)\left(1 - \exp\left(-\frac{T_c^p}{\xi T_{2,l}}\right)\right).$$

Note that in the limit $v \to 0$ the summations in Eqs. (40b) and (40c) vanish and the derivative in Eq. (40) reduces to the expression in Eq. (22) for a stationary tool.

The derivatives with respect to $\eta_k$ for k=1, . . . , $N_o$ for a moving tool are given by, $$-\frac{\partial \ln L(\vec{x})}{\partial \eta_k} = \tag{41}$$

$$-\sum_{p=1}^{N} \sum_{m=1}^{N_w(p)} \frac{(\tilde{I}_m^p - I_m^p(\vec{x}))}{\Psi_p \hat{\sigma}_{m,p}^2}\left[b_k F_{m,p}\left(\frac{TE_p(c\eta_k^2 + d_p)}{\eta_k}\right)\right]$$

-continued $$\left\{W_p c \exp(-W_p c \eta_k) \left(\frac{l_{ant} - vT_c^p}{l_{ant}}\right) - \frac{vT_c^p}{l_{ant}\eta_k}\right.$$

$$\exp\left(-\left(\frac{l_{pol}}{v} + T_c^p\right) c \eta_k\right) + \left(\frac{v}{l_{ant} c \eta_k^2} + \frac{l_{pol}}{l_{ant}\eta_k}\right)$$

$$\exp\left(-\frac{l_{pol} c \eta_k}{v}\right) (1 - \exp(-(T_c^p c \eta_k))) +$$

$$b_k f_k(v) F'_{m,p}\left(\frac{TE_p(c\eta_k^2 + d_p)}{\eta_k}\right) \frac{TE_p(c\eta_k^2 - d_p)}{\eta_k^2}\right].$$

In the limit v→0 the derivatives in Eq. (4 1) reduce to those in Eq. (29) for a stationary tool. The function $f_k(v)$ in the last term is the speed dependent polarization function for the crude oil constituent viscosities. It is obtained by replacing $T_1$ with $(c\eta_k)^{-1}$ everywhere in Eq. (39).

Monte Carlo Simulations for Moving Tool

The speed dependent polarization correction was implemented in the inversion of the relaxation model in Eq. (1) and Monte Carlo simulations were conducted for a model formation to test the inversion. A suite of synthetic spin-echo data was generated for a model tool with an antenna length $l_{ant}$=18 inches, a magnet pre-polarization length $l_{pol}$=36 inches and for constant logging tool speeds of 1200 and 1800 feet per hour. The data were generated using the full relaxation model in Eq. (A.1) of Appendix A for a formation containing brine, crude oil, gas and OBMF. The brine $T_2$-distribution used for the simulations is shown in FIG. 8. The simulations assumed a formation temperature of 100 degrees Celsius. The hydrogen index of all liquids is assumed to be equal to 1 and the hydrogen index of the gas is assumed to be equal to 0.5. Random noise with a standard deviation equal to 4.0 p.u. was added to each echo. To reduce the noise and simulate depth log stacking, echo sequences were repeated and averaged. The number of repeats for each measurement is shown in Table 7. The two dead times for the first measurement which is non-overlapping were selected so that the tool moves one antenna length during the cycle time. All other measurements are overlapping. FIG. 11 shows the measurement suite used for the Monte Carlo simulation, and FIG. 12 shows comparison of actual fluid saturations and oil viscosity with the Monte Carlo estimates.

TABLE 7

Measurement Parameters for Monte Carlo Simulation @ 1200 and 1800 feet/hour

| Measurement | TE (ms) | W (s) | G (Gauss/cm) | J | Repeats |
|---|---|---|---|---|---|
| 1 | 0.2 | 3.9 (2.4) | 25 | 3000 | 6 |
| 2 | 0.3 | 1.0 | 25 | 600 | 6 |
| 3 | 0.6 | 0.45 | 25 | 600 | 6 |
| 4 | 1.0 | 0.3 | 25 | 100 | 6 |
| 5 | 2.0 | 0.15 | 25 | 100 | 45 |
| 6 | 4.0 | 0.1 | 25 | 100 | 45 |

Effects of Logging Speed on T2 Relaxation Times

In addition to the effects of tool motion on polarization functions (T1 speed effect) there is also an apparent increased transverse relaxation rate (T2 speed effect) due to tool motion. The T2 speed effect occurs because there is a loss of transverse magnetization during a CPMG because the r.f. antenna moves away from the formation interval that was excited by the 90-degree pulse. If the T2 speed effect is not accounted for then the longer T2 relaxation times recovered by the inversion will be suppressed compared to their actual values.

The following model has accounted for this effect. Let $\Delta M_t$ be the change in transverse magnetization opposite the r.f. antenna in a time interval $\Delta t$ due to tool motion. Then, $$\Delta M_t \cong -\frac{v\Delta t}{L} M_t, \tag{42}$$

where L is the antenna length and v is the logging speed. The above equation is an approximation because it assumes that the transverse magnetization is uniform over the antenna. Rearranging Eq. (42) and taking the limit $\Delta t \to 0$ one finds that, $$\left(\frac{\partial M_t}{\partial t}\right)_v = -\frac{v}{L} M_t \equiv -\frac{M_t}{T_{2,v}}, \tag{43}$$

where the relaxation rate due to tool motion has been defined, i.e., $$\frac{1}{T_{2,v}} = \frac{v}{L}. \tag{44}$$

The relaxation rates are additive so that the T2 speed effect is easily incorporated into the relaxational model. That is, one simply adds the term shown in the above equation to all equations for transverse relaxation rates. The T2 effect has been incorporated into the T2-relaxational model (e.g., see Eq. (1)). The main result is the modification of the sensitivity functions defined in Eqs. (16)–(18).

Appendix A: Extension of the Method to Include Gas

The model in Eq. (1) is easily modified to include a gas signal, i.e., $$A_j^p = \sum_{l=1}^{N_s} a_l \exp\left(-\frac{j*TE_p}{T_{2,l}^\dagger(p)}\right)\left(1 - \exp\left(-\frac{W_p}{\xi * T_{2,l}}\right)\right) + \tag{A.1}$$

$$\sum_{k=1}^{N_o} b_k \exp\left(-\frac{j*TE_p}{T_{2,o}^\dagger(\eta_k, p)}\right)\left(1 - \exp\left(-\frac{W_p}{T_{1,o}(\eta_k)}\right)\right) +$$

$$A_{OBMF} \exp\left(-\frac{j*TE_p}{T_{2,OBMF}^\dagger(p)}\right)\left(1 - \exp\left(-\frac{W_p}{T_{1,OBMF}}\right)\right) +$$

$$A_g \exp\left(-\frac{j*TE_p}{T_{2,g}^\dagger(p)}\right)\left(1 - \exp\left(-\frac{W_p}{T_{1,g}}\right)\right)$$

where $A_g$ is the amplitude of the gas signal. The apparent gas relaxation rate is, $$\frac{1}{T_{2,g}^\dagger(p)} = \frac{1}{T_{2,g}*(P,T)} + \frac{(\gamma_H * G_p * TE_p)^2}{12} D_g(P,T), \tag{A.2}$$

where the gas relaxation rates in zero gradient, $T_{1,g}(P,T) = T_{2,g}(P,T)$, and the gas diffusion constant $D_g(P,T)$ are functions of formation temperature and pressure and can be estimated from published data (Kleinberg et al., 1996, supra). The inversion of a suite of multi frequency data using the model in Eq. (A.1) can be done using the method developed in this report. The amplitude of the gas signal ($A_g$) is determined from the maximum likelihood estimation. The gas-filled porosity is computed using Ag and the gas hydrogen index $HI_g(P,T)$ which can be estimated from published correlations. Gas should be easier to detect than crude oil because the gas diffusion constant is roughly an order of magnitude greater than that of the brine whereas the diffusion constant of crude oil, depending on its viscosity, can be comparable to that of brine. Using the full model with the gas term leads to obvious modifications to Eqs. (11)–(14), i.e., the gas filled porosity ($\phi_g$) is defined by, $$\phi_g = \frac{1}{HI_g} A_g, \quad (A.3)$$

and oil and gas saturations are computed by analogy with Eq. (14), e.g., $$S_o(r) = \frac{\phi_o}{\phi_w + \phi_o + \phi_g + \phi_{obmf}} \equiv \frac{\phi_o}{\phi_T}, \quad (A.4)$$

for the oil saturation and, $$S_g(r) = \frac{\phi_g}{\phi_w + \phi_o + \phi_g + \phi_{obmf}} \equiv \frac{\phi_g}{\phi_T}, \quad (A.5)$$

for the gas saturation.

The following two examples demonstrate the application of the method to gas detection. The first example is for a gas reservoir drilled with an oilbase mud. Noisy spin-echo data were generated using the six measurements in Table I for both examples. The first example is for a formation containing brine and gas only, i.e., the radius of invasion of the OBMF is less than the DOI of the measurements. The gas relaxation time, gas hydrogen index and gas diffusion constant used for both examples in this Appendix are respectively, $T_{1,g}$=4.5 s, $HI_g$=0.5 and $D_g$=8.0E−4 cm$^2$/s. The inputs and inversion results for the first gas example are shown in Table A.1. Note that the results represent a single sample.

TABLE A.1

Brine and Gas Filled Formation
Inputs:
$\phi_o$ = 0 p.u., $\phi_{OBMF}$ = 0 p.u., $\phi_w$ = 20 p.u., $\phi_g$ = 10 p.u., $\phi_T$ = 30 p.u., $S_g$ = 0.33, $\xi$ = 1.5

| Noise Per Echo | $\sqrt{\Psi}$ = 2.0 p.u. | $\sqrt{\Psi}$ = 4.0 p.u. |
|---|---|---|
| $\hat{\xi}$ | 1.6 | 1.4 |
| $\hat{S}_g$ | 0.35 | 0.29 |
| $\hat{S}_o$ | 3.4E−4 | 6.4E−3 |
| $\hat{\phi}_g$ | 10.3 | 7.8 |
| $\hat{\phi}_T$ | 29.6 | 28.0 |
| $\hat{\phi}_o$ | 1.0E−2 | 0.18 |
| $\hat{\phi}_w$ | 19.3 | 20.0 |
| $\hat{\phi}_{OBMF}$ | 9.1E−3 | 1.3E−5 |

The results in Table A.1 show that method can be used to accurately evaluate gas reservoirs. The second example is for a reservoir containing three fluids, i.e., brine, OBMF and gas. The inputs and the results of the inversion are shown in Table A.2.

TABLE A.2

Brine, OBMF and Gas Filled Formation
Inputs:
$\phi_o$ = 0 p.u., $\phi_{OBMF}$ = 10 p.u., $\phi_w$ = 10 p.u., $\phi_g$ = 10 p.u., $\phi_T$ = 30 p.u., $S_o$ = 0, $S_g$ = 0.33, $\xi$ = 15

| Noise Per Echo | $\sqrt{\Psi}$ = 2.0 p.u. | $\sqrt{\Psi}$ = 4.0 p.u. |
|---|---|---|
| $\hat{\xi}$ | 2.0 | 1.5 |
| $\hat{S}_g$ | 0.32 | 0.28 |
| $\hat{S}_o$ | 0.086 | 0.01 |
| $\hat{\phi}_g$ | 9.5 | 8.0 |
| $\hat{\phi}_T$ | 29.6 | 28.2 |
| $\hat{\phi}_o$ | 2.56 | 0.29 |
| $\hat{\phi}_w$ | 7.3 | 9.8 |
| $\hat{\phi}_{OBMF}$ | 10.2 | 10.1 |

The results in Table A.2 show that it is possible to correctly evaluate a gas reservoir invaded by OBMF. Since the OBMF filled porosity is accurately computed the gas saturation in the undisturbed zone can be computed if the reservoir is at residual water saturation (i.e., if the OBMF displaces only gas).

Appendix B: Why Crude Oils Have A Distribution of Diffusion Constants

This Appendix shows, using a simple model based on the Langevin equation, why there exists a distribution of self-diffusion constants in the crude oil mixture. The assumption in eq. (10a) that the self-diffusion constants are inversely proportional to the constituent viscosities is shown to follow naturally from solution of the Langevin equation.

The Langevin equation is commonly used to study the Brownian motion of a particle in a homogeneous liquid. It is a stochastic classical equation of motion for a "single particle" in a many-particle system. Two effects describe the molecular interactions with all the other particles in the system. The first effect is a frictional force or viscous like resistance to motion. This is the average effect of the other particles. On a very short time scale compared to the mean collision time there is also a randomly fluctuating force produced by the rapid motions of the other particles. The Langevin equation has a firm microscopic basis and can be derived from a many-particle Hamiltonian (Forster, 1975) that includes the effects of molecular interactions.

Let $x_k(t)$ be the x-coordinate at time t of component k in the crude oil mixture. A component is any one of the hydrocarbon molecules that is contained in the mixture. On a molecular level each component due to differences in size, composition, shape and mass will have different interactions with the other constituents. As a result each component will have a different self-diffusion coefficient that depends on its local environment. The self-diffusion constant $D_k$ of component k can be defined in terms of the mean squared displacement of the particle at time t (for motion in one-dimension), $$D_k = \frac{\langle (x_k(t) - x_k(0))^2 \rangle}{2t}. \quad (B.1)$$

The angular brackets in the above equation denote a statistical average over an ensemble of identically prepared systems. For the sake of notational simplicity one-dimensional motion is considered. The generalization of the results to three dimensions is transparent. For example, the factor of 2 in the denominator of (B.1) is changed to a factor of 6 in three-dimensions because all directions are on an equal footing, i.e., there is no preferred direction for diffusion in the model. The Langevin equation of motion can be written in the form, $$M_k \ddot{x}_k + M_k \zeta_k \dot{x}_k = F_k(t), \quad (B.2)$$

where $M_k$ is the mass of the particle. The dots are used to denote time derivatives. The second term is a frictional force that accounts for the average effect of the intermolecular interactions on the diffusing particle. For convenience in the subsequent calculations the particle mass has been included in the frictional force. Note that the friction parameter $\zeta_k$ has the dimensions of inverse time. The function $F_k(t)$ is a zero mean random force with auto-correlation function given by, $$\langle F_k(t) F_k(t') \rangle = 2 k_B T M_k \zeta_k \delta(t-t'), \quad (B.3)$$

where $k_B$ is Boltzmann's constant, T is the temperature in degrees Kelvin and $\delta(t-t')$ is the Dirac delta function. The constant multiplying the Dirac function is not arbitrary. It was chosen to guarantee that the solutions of the Langevin equation have the correct equilibrium statistical mechanical properties, e.g., the equipartition theorem requires that, $$\langle \dot{x}_k^2 \rangle = \frac{k_B T}{M_k}. \quad (B.4)$$

Equation (B.3) is sometimes referred to as a fluctuation-dissipation theorem in the field of non-equilibrium statistical mechanics. A general solution of the Langevin equation (B.2) with the initial conditions, $x_k(0)=0$ and $\dot{x}_k(0)=0$ is obtained by double integration, $$x_k(t) = \frac{1}{M_k} \int_0^t dt' \int_0^{t'} d\tau F_k(\tau) \exp(-\zeta_k(t' - \tau)). \quad (B.5)$$

The double integral in (B.5) can be reduced to a single integral by performing integration by parts on the outer integral. One finds that, $$x_k(t) = \frac{1}{M_k \zeta_k} \int_0^t d\tau F_k(\tau)(1 - \exp(-\zeta_k(t - \tau))). \quad (B.6)$$

Indeed, differentiation of (B.6) shows that it satisfies both (B.2) and the initial conditions. The mean squared displacement of the particle is calculated by squaring (B.6) and taking statistical averages, e.g., $$\langle x_k^2(t) \rangle = \frac{1}{(M_k \zeta_k)^2} \int_0^t d\tau_1 \int_0^t d\tau_2 [1 - \exp(-\zeta_k(t - \tau_1))] \quad (B.7)$$
$$[1 - \exp(-\zeta_k(t - \tau_2))] \langle F_k(\tau_1) F_k(\tau_2) \rangle.$$

The integrals in (B.7) are easily performed by recalling eq. (B.3) and using the properties of the Dirac delta function. One finds that, $$\langle x_k^2(t) \rangle = \frac{2 k_B T}{M_k \zeta_k} \left[ t - \frac{2}{\zeta_k}(1 - \exp(-\zeta_k t)) + \frac{1}{2\zeta_k}(1 - \exp(-2\zeta_k t)) \right]. \quad (B.8)$$

In the long time limit, i.e., for $\zeta_k t > 1$ the mean square displacement in (B.8) reduces to a steady state solution given by, $$\langle x_k^2(t) \rangle = \frac{2 k_B T}{M_k \zeta_k} t \equiv 2 D_k t. \quad (B.9)$$

Therefore the self-diffusion constant for the k-th component in the mixture is given by, $$D_k = \frac{k_B T}{M_k \zeta_k}, \quad (B.10)$$

which is called an Einstein relation. In a crude oil there are a distribution of diffusion constants because of the different kinds of molecules in the mixture. A pulse field gradient measurement of the diffusion constant distribution in a crude oil would probably yield a broad distribution with few if any distinct peaks. For a spherical particle of radius a diffusing in a homogeneous liquid with viscosity $\eta$ Stokes showed that, $M\zeta = 6\pi a \eta$. Combining the Stokes relation with the Einstein relation one obtains the well-known Einstein-Stokes diffusion constant, i.e., $$D = \frac{k_B T}{6 \pi a \eta} \text{ (Einstein-Stokes Equation)}. \quad (B.11)$$

In analogy with the Stokes relation it is plausible to assume that for each component in the crude oil mixture that $M_k \zeta_k = C \eta_k$ where the $\eta_k$ are the constituent viscosities introduced in Eqs. (5) and (10a) and where C is a proportionality constant that depends on some average size parameter. That is, the constituent viscosities are proportional to the friction parameters. Using (B.10) this leads directly to an equation that has the same functional form as Eq. (10a).

Appendix C: Alternative Parametrizations of the Relaxational Model

It will be evident that other parameterizations of the relaxational model in Eq. (1) are possible and might be desirable for specific applications. For example, the transverse relaxation times (in zero field gradient) and diffusion constants in the crude oil relaxational model in Eq. (1) can in analogy with the brine relaxation term be parameterized by a distribution of logarithmically spaced relaxation times (other spacings, of course, are also possible). That is, one introduces a set of crude oil relaxation times, $$T_{2,o}(k) = T_{2,\min}^{(o)} \left( \frac{T_{2,\max}^{(o)}}{T_{2,\min}^{(o)}} \right)^{\frac{k-1}{N_o - 1}} \equiv \frac{T}{a\eta_k} \text{ for } k = 1, \cdots, N_o, \quad (C.1)$$

where $T_{2,\min}^{(o)}$ and $T_{2,\min}^{(o)}$ are the minimum and maximum values, respectively, of the crude oil relaxation time distribution. In this picture the $\eta_k$ are specified by the relaxation times. The crude oil longitudinal relaxation times can be parameterized by the same set of logarithmically spaced relaxation times, i.e., $$T_{1,o}(k) = \xi_{oil} T_{2,o}(k), \quad (C.2)$$

where $\xi_{oil} \leq 1$ is a parameter that accounts for crude oils that have unequal transverse and longitudinal relaxation times. For crude oils that have been measured, $\xi_{oil} \cong 1$. The diffusion constants in Eq. (3) can also be parameterized in terms of the logarithmically spaced relaxation times since by combining Eqs (5) and (10a) and the above equations one finds, $$D_o(k) = a b T_{2,o}(k) = \frac{bT}{\eta_k}. \quad (C.3)$$

The above parameterization reduces the number of unknowns in the crude oil relaxation term in Eq. (1) from $2N_o$ to $N_o$. Moreover the problem is more linear since the unknowns are the set of amplitudes $\{b_k\}$. Once the $\{b_k\}$ are determined by fitting the data, the macroscopic viscosity is determined from Eq. (8).

The introduction of the constituent viscosities depends, in part, on the validity of the constitutive relations in Eqs. (5) and (10). An approach to the inversion of Eq. (1) that does not depend upon the constitutive relations is to consider the No crude oil relaxation times ($T_{2,o}(\eta_k)$) and the $N_o$ diffusivities ($D_o(\eta_k)$) as independent parameters in the model. The downside of this approach is twofold: (1) it increases the number of unknowns by $N_o$ and (2) the parameters $T_{2,o}(\eta_k)$ and $D_o(\eta_k)$ by themselves, without a link to viscosity, provide less useful reservoir evaluation information.

Appendix D: Powell's Nonlinear Constrained Optimization Algorithm

This Appendix provides a general overview an algorithm and subroutine developed by M. J. D. Powell can be used to minimize the function in Eq. (15) hereof. The function to be minimized is referred to as the objective function. The minimization of the objective function falls into a general class known as linearly constrained non- linear optimization problems. In this class of problems, the objective function depends non-linearly on all or some of the variables and the variables are subject to linear equality and/or inequality constraints. The latter include simple bounds on the variables, e.g., upper and lower limits that are imposed by the physics of the problem. The minimization of Eq. (15) falls into this class and the problem can be stated as follows:

$$\min f(x)$$
$$x \in R^n$$
$$\text{subject to } x_l \leq x \leq x_u \quad \text{(D.1)}$$

Here the upper and lower bounds represent physical bounds on the model parameters in the relaxational models shown in Eqs. (1) and (A.1), e.g., the constituent viscosities, the fluid amplitudes, and the apparent brine T1/T2 ratio. The minimization method is iterative and the algorithm employed on the data suites used in the examples hereof and discussed in this Appendix and in conjunction with FIG. 7 hereof was developed by Powell (1989) (hereafter referred to as the Powell algorithm) and is part of the commercially available IMSL library of subroutines licensed by the Visual Numerics Corp. (Houston, Tex.). The implementation of the Powell algorithm used for the computations described herein is the double precision version of the IMSL subroutine called DLCONG and it was used to perform the simulations shown herein. It will be understood that other different non-linear optimization algorithms (see e.g. Schittkowski, K., NLPQL: A Fortran Subroutine Solving Constrained Nonlinear Programming Problems, published in the Annals of Operations Research, vol. 5, pp. 485–500, 1985) can also be used to effect the constrained minimization of a nonlinear objective function.

The first step is to set the upper and lower bounds and initial values (denoted in this Appendix by the vectors, $x_u, x_l, x^0$) for all of the variable parameters in the objective function. The algorithm is said to be globally convergent so that a feasible (i.e., one that satisfies the constraints) solution can be found regardless of the starting value. It should be noted that if a non-linear objective function is not strictly convex, e.g., has several local minima in the feasible region then different initial values for the parameters can lead to solutions that are not a global minimum. In such cases, one procedure for finding a global minimum is to employ a grid of initial values and then select the global minimum from the family of solutions, i.e., it is the solution that corresponds to the smallest value of the objective function.

In the Powell algorithm, at each iteration, the objective function is approximated by a quadratic function and a search direction for the next iteration is found by solving a quadratic programming (QP) problem. For example, let xk be the k-th iterate and consider the QP problem:

$$\min [f(x^k) + d_k^T \nabla f(x^k) + \tfrac{1}{2} d_k^T B^k d_k]$$
$$\text{subject to: } c^T d \leq 0. \quad \text{(D.2)}$$

The vector c is selected to be a vector of ones (e) to satisfy the upper bound constraint $x_i \leq x_u$ axe and $(-e)$ to satisfy the lower bound constraint $-x_i \leq -x_l$. The QP problem is solved by the Karush-Kuhn-Tucker (KKT) theorem (see e.g., Peressini, A. L., Sullivan R. E. and Uhl, The Mathematics Of Nonlinear Programming, Springer Verlag Publishing Company, New York, Chapter 5, 1988) to determine the search direction vector $d_k$ and a vector of Lagrange multipliers $\lambda_k \leq 0$ for the active constraints (e.g., for the variables on the constraint boundaries). The matrix $B^k$ is a positive definite approximation to the second derivative matrix of the objective function at the k-th iteration. After the search direction $d_k$ is found, a line search is performed to determine the step size $\alpha_k$ for the next iteration. The new point, $x^{k+1} = x^k + \alpha^k d^k$ is required to satisfy the conditions:

$$f(x^{k+1}) \leq f(x^k) + 0.1 \alpha^k (d^k)^T \nabla f(x^k) \quad \text{(D.3)}$$

and, $$(d^k)^T \nabla f(x^{k+1}) \geq 0.7 (d^k)^T \nabla f(x^k). \quad \text{(D.4)}$$

The second derivative matrix $B^k$ is updated by the BFGS method (see e.g., Peressini, Sullivan and Uhl, 1988, supra). The iterations continue until the two-norm of the KKT residual vector is less than a user supplied convergence parameter, i.e., $$\left\| \nabla f(x^k) - \sum_{i=1}^{n_a} \lambda^k a^k \right\|_2 \leq acc \quad \text{(D.5)}$$

where $a^k$ are unit vectors in the parameter space for the active constraints at iteration k and acc is a user supplied accuracy parameter. Termination of the algorithm can also occur if successive iterates fail to decrease the objective function.

Appendix E: Effects of Internal Rock Gradients On Inversion

In the foregoing, the magnetic field gradients have been assumed to be solely due to spatial variations in the applied magnetic field. In porous rocks containing fluids it is known that differences in magnetic susceptibilities of the pore fluids and the rock matrix can give rise to internal gradients in the rock (Hurlimann, Martin D., Effective Gradients In Porous Media Due To Susceptibility Differences, Journal of Magnetic Resonance, 131, pp. 232–240, 1998 ). The internal gradients are induced by the applied field and will exist even if the applied magnetic field is perfectly homogeneous. The local internal gradient $G_{int}(\vec{r})$ at position $\vec{r}$ is proportional to the strength of the applied field, $B_0(\vec{r})$, i.e., $$G_{int}(\vec{r}) \cong \frac{\Delta \chi(\vec{r}) B_0(\vec{r})}{a(\vec{r})}, \quad \text{(E.1)}$$

where $\Delta_\chi$ is the local susceptibility difference between the pore fluids and the rock grains and $a(\vec{r})$ is an average local pore size. The distribution of internal gradients within rocks is not known. However, theoretical arguments suggest that the gradients are localized close to the pore surfaces and are strongest in the smaller pores. It is possible that internal gradient effects will have little if any effect on the determination of hydrocarbon saturations and oil viscosity.

Nevertheless, it is helpful to include a method for estimating and incorporating such effects that might occur under some field conditions. It is shown in this Appendix that an effective internal gradient can be estimated in each measurement shell from suites of NMR data and that its effects can be included in the inversion. The idea behind the method is that the internal gradient effects can be included in the multi-fluid T2-relaxational model (e.g., Eq. 1) by replacing the applied tool gradient by an effective total gradient. Let an effective total gradient be defined as the sum of the applied tool gradient and the internal rock gradient, i.e., $$G_t(\vec{r}) \cong G_a(\vec{r}) + \left\langle \frac{\Delta \chi(\vec{r})}{a(\vec{r})} \right\rangle_\Omega B_0(\vec{r}), \tag{E.2}$$

where the angular brackets denotes a volume average over the macroscopic measurement volume ($\Omega$), e.g., the volume of a set of closely spaced measurement shells corresponding to a suite of data. The quantity in brackets has the dimensions of an inverse length which is henceforth denoted by the parameter $\lambda$ so that the above equation can be written, $$G_t(\vec{r}) \cong G_a(\vec{r}) + \lambda B_0(\vec{r}). \tag{E.3}$$

An average internal gradient is determined by estimating the unknown parameter $\lambda$ from the NMR data, i.e., $$G_{int}(\vec{r}) = \lambda B_0(\vec{r}). \tag{E.4}$$

To estimate $\lambda$ from a suite of NMR data replace the applied tool gradients ($G_p$) in the multi-fluid T2-relaxational model (e.g., see Eqs. 1–3) by the total gradient, $$G_t(p) = G_p + \lambda B_0(\vec{r}_p), \tag{E.5}$$

for p=1, N where N is the number of measurements in the suite of NMR measurements. $G_p$ and $B_0(\vec{r}_p)$ are the tool gradient and applied magnetic field for measurement p. The logarithm of a modified maximum likelihood function analogous to Eq. 15 can be constructed from the multi-fluid T2-relaxational model containing the total gradient. The internal gradient parameter $\lambda$ becomes an additional parameter in the model to be determined by the inversion. Analytical derivatives of the logarithm of the modified likelihood function with respect to $\lambda$ have been computed to facilitate the inversion. The main idea here is that the multi-frequency NMR data contains information on the internal gradients and therefore the data itself can be used to self-consistently estimate the gradients. Moreover, this approach accounts for the effects of the gradients on the inversion results. Although this Appendix has discussed a specific model (Eqs., E.1–E.5) for representing the total gradient it is understood that any other physical model of the latter can be used in the multi-fluid T2-relaxational model.

Appendix F: Determining Fluid Saturation Distributions in Partially Saturated Laboratory Core Samples In laboratory studies of the physical properties of porous rocks it is often desirable to saturate the rocks with oil (or other fluid) and water to simulate native state conditions in petroleum reservoirs. Of key importance in determining the physical properties of the partially saturated rock sample is accurate determination of the oil saturation. The oil typically has to be forced into a sample by centrifuge starting with an initially brine saturated state. The problem of determining an accurate final oil saturation is well known. There are established techniques used in practice such as "differential weight measurements" (DWM) that are commonly used to estimate oil saturations. Oil saturations are estimated from the DWS method using the equation, $$\hat{S}_{oil} = \frac{\Delta W}{\phi V (\rho_w - \rho_{oil})}, \tag{F.1}$$

where $\Delta W$ is the difference in weight of the fully brine saturated sample and the partially saturated sample, @ is the porosity of the sample, v is the sample volume, $\rho_w$ is the brine density and $\rho_{oil}$ is the oil density.

The DWM method has recognized limitations and shortcomings. First, it provides an average saturation for the whole sample. In practice the saturation will vary throughout the sample because of rock heterogeneity and centrifuge pressure differences in the sample. Other techniques such as resistivity scans of the sample can be used in conjunction with Archie's equation to estimate fluid saturations. This technique has limited accuracy because of the approximate nature of Archie's equation and its dependence on saturation exponents and formation factors which are frequently not accurately known.

An above-ground application of the technique hereof provides an NMR method that can be used to determine local fluid saturations in relatively thin sample slices rather than an average saturation (e.g. according to the above-summarized DWM method). It provides a "saturation image" along the sample length. The technique hereof does not even require knowledge of the sample porosity (i.e., the NMR computed saturations are determined from ratios). Because the method provides a direct measurement of saturation, it avoids the problems of resistivity scans which require use of an approximate auxiliary equation.

What is claimed is:

1. A method for determining properties of earth formations surrounding a borehole, comprising the steps of:
    (a) providing a logging device that is moveable through the borehole;
    (b) transmitting electromagnetic energy from said logging device into the formations, and receiving nuclear magnetic resonance spin echoes at said logging device;
    (c) performing step (b) a plurality of times, with a respective plurality of different transmitting and/or receiving conditions to obtain a plurality of measurements;
    (d) generating a formation model that includes a plurality of model components for a brine phase and a plurality of model components for a native oil phase;
    (e) modifying the model components to optimize the model with respect to the measurement signals; and
    (f) outputting model components of the optimized model.

2. The method as defined by claim 1, wherein said step of modifying the model components comprises iteratively modifying said model components for the brine phase and model components for the native oil phase to optimize correspondence between model signals derived from the model and said measurement signals.

3. The method as defined by claim 1, wherein said step of generating a formation model comprises generating a model that further includes an oil base mud filtrate component.

4. The method as defined by claim 1, wherein said step of generating a formation model comprises generating a model that further includes a gas component.

5. The method as defined by claim 3, wherein said step of generating a formation model comprises generating a model that further includes a gas component.

6. The method as defined by claim 1, wherein said step of transmitting electromagnetic energy from said logging device and receiving nuclear magnetic resonance spin echoes at said logging device includes producing a static magnetic field in a region of investigation and generating sequences of magnetic field radio frequency pulses in the region of investigation and receiving sequences of nuclear magnetic resonance spin echoes, and wherein the applied static magnetic field gradient in the investigation region is $G_p$, and wherein the wait time between sequences is $W_p$, and the echo spacing is $TE_p$, and the number of received spin echoes of a sequence is $J_p$, and wherein said step (c) comprises performing step (b) a plurality of times with respective different values of at least one condition selected from the group consisting of $G_p$, $W_p$, $TE_p$, and $J_p$.

7. The method as defined by claim 2, wherein said step of transmitting electromagnetic energy from said logging device and receiving nuclear magnetic resonance spin echoes at said logging device includes producing a static magnetic field in a region of investigation and generating sequences of magnetic field radio frequency pulses in the region of investigation and receiving sequences of nuclear magnetic resonance spin echoes, and wherein the applied static magnetic field gradient in the investigation region is $G_p$, and wherein the wait time between sequences is $W_p$, and the echo spacing is $TE_p$, and the number of received spin echoes of a sequence is $J_p$, and wherein said step (c) comprises performing step (b) a plurality of times with respective different values of at least one condition selected from the group consisting of $G_p$, $W_p$, $TE_p$, and $J_p$.

8. The method as defined by claim 7, wherein said step (c) comprises performing step (b) N times to obtain a suite of N measurements.

9. The method as defined by claim 8, wherein each of said measurements includes several repetitions of the pulse-echo sequences, and wherein said measurements comprise detection of spin echo amplitudes during the sequences.

10. The method as defined by claim 8, wherein the measurements p are taken at a plurality of respectively separate measurement region shells.

11. The method as defined by claim 10, wherein said shells are substantially cylindrical shells having radial extents of about 1 mm.

12. The method as defined by claim 1, wherein said step (d) of generating a formation model includes generating a set of model amplitude components that define the transverse relaxation time distribution of the brine phase, and a further set of model amplitude components that define the transverse relaxation time distribution of the native oil, and a further set of model components that define the constituent viscosities of the native oil.

13. The method as defined by claim 2, wherein said step (d) of generating a formation model includes generating a set of model amplitude components that define the transverse relaxation time distribution of the brine phase, and a further set of model amplitude components that define the transverse relaxation time distribution of the native oil, and a further set of model components that define the constituent viscosities of the native oil.

14. The method as defined by claim 7, wherein said step (d) of generating a formation model includes generating a set of model amplitude components that define the transverse relaxation time distribution of the brine phase, and a further set of model amplitude components that define the transverse relaxation time distribution of the native oil, and a further set of model components that define the constituent viscosities of the native oil.

15. The method as defined by claim 12, wherein said step (d) of generating a formation model further includes generating a model component that represents the apparent ratio of brine longitudinal relaxation time to transverse relaxation time.

16. The method as defined by claim 3, wherein said step (d) of generating a formation model includes generating a set of model amplitude components that define the transverse relaxation time distribution of the brine phase, and a further set of model amplitude components that define the transverse relaxation time distribution of the native oil, and a further set of model components that define the constituent viscosities of the native oil, and a model component that defines an oil base mud filtrate amplitude.

17. The method as defined by claim 16, wherein said step (d) of generating a formation model further includes generating a model component that represents the apparent ratio of brine longitudinal relaxation time to transverse relaxation time.

18. The method as defined by claim 1, further comprising the step of deriving, from the output model components, at least one porosity from the group consisting of water-filled porosity, oil-filled porosity and total NMR-filled porosity of the formations.

19. The method as defined by claim 14, further comprising the step of deriving, from the output model components, at least one porosity from the group consisting of water-filled porosity, oil-filled porosity and total NMR-filled porosity of the formations.

20. The method as defined by claim 3, further comprising the steps of deriving, from
the output model components, the oil base mud filtrate-filled porosity of the formations.

21. The method as defined by claim 4, further comprising the step of deriving, from the output model components, the gas-filled porosity of the formations.

22. The method as defined by claim 1, further comprising the step of deriving, from the output model components, the free fluid porosity of the formations.

23. The method as defined by claim 1, further comprising the step of deriving, from the output model components, the bound fluid porosity of the formations.

24. The method as defined by claim 1, further comprising the step of deriving, from the output model components, at least one saturation from the group consisting of water saturation and oil saturation of the formations.

25. The method as defined by claim 14, further comprising the step of deriving, from the output model components, at least one saturation from the group consisting of water saturation and oil saturation of the formations.

26. The method as defined by claim 3, further comprising the step of deriving, from the output model components, the oil base mud filtrate saturation of the formations.

27. The method as defined by claim 4, further comprising the step of deriving, from the output model components, the gas saturation of the formations.

28. The method as defined by claim 12, further comprising the step of deriving, from the output model components, the viscosity of the native oil of the formations.

29. The method as defined by claim 12, further comprising the step of deriving, from the output model components, the diffusion constants of the native oil constituents of the formations.

30. The method as defined by claim 12, further comprising the step of deriving, from the output model components, the relaxation times of the native oil constituents of the formations.

31. The method as defined by claim 14, further comprising repeating said method for different separated regions of investigation in the formations, and further comprising the step of deriving, from the output model components for the different separated regions of investigation, a fluid saturation profile of the formations.

32. The method as defined by claim 14, further comprising repeating said method for different separated regions of investigation in the formations, and further comprising the step of deriving, from the output model components for the different separated regions of investigation, a fluid saturation profile of the formations.

33. The method as defined by claim 7, wherein the measurements of steps (b) and (c) are taken while said logging device is moving through the borehole at a velocity v, and wherein said model signals are derived from the model based on computed magnetic resonance polarization functions which depend on wait time Wp and the velocity v.

34. The method as defined by claim 33, wherein both longitudinal polarization functions and transverse relaxation times of the formation model are modified as a function of said velocity, v.

35. The method as defined by claim 6, wherein the magnetic field gradient in a measurement region of the formations includes a component for the applied gradient Gp and a component for internal gradient in said measurement region of the formations resulting from magnetic susceptibility contrasts therein.

36. A method for determining properties of earth formations surrounding a borehole containing oil base mud, comprising the steps of.

(a) providing a logging device that is moveable through the borehole;

(b) transmitting electromagnetic energy from said logging device into the formations, and receiving nuclear magnetic resonance spin echoes at said logging device;

(c) performing step (b) a plurality of times, with a respective plurality of different transmitting and/or receiving conditions to obtain a plurality of measurements;

(d) generating a formation model that includes model components for a brine phase, a native oil phase, and an oil base mud filtrate phase;

(e) modifying the model components to optimize the model with respect to the measurement signals; and (f) outputting model components of the optimized model.

37. The method as defined by claim 36, wherein said step of modifying the model components comprises iteratively modifying said model components for the brine phase, the native oil phase, and the oil base mud filtrate phase to optimize correspondence between model signals derived from the model and said measurement signals.

38. The method as defined by claim 36, wherein said step of generating a formation model comprises generating a model that further includes a gas component.

39. The method as defined by claim 37, wherein said step of transmitting electromagnetic energy from said logging device and receiving nuclear magnetic resonance spin echoes at said logging device includes producing a static magnetic field in a region of investigation and generating sequences of magnetic field radio frequency pulses in the region of investigation and receiving sequences of nuclear magnetic resonance spin echoes, and wherein the applied static magnetic field gradient in the investigation region is $G_p$, and wherein the wait time between sequences is $W_p$, and the echo spacing is $TE_p$, and the number of received spin echoes of a sequence is $J_p$, and wherein said step (c) comprises performing step (b) a plurality of times with respective different values of at least one condition selected from the group consisting of $G_p$, $W_p$, $TE_p$, and $J_p$.

40. The method as defined by claim 39, wherein said step (c) comprises performing step (b) N times to obtain a suite of N measurements.

41. The method as defined by claim 40, wherein each of said measurements includes several repetitions of the pulse-echo sequences, and wherein said measurements comprise detection of spin echo amplitudes during the sequences.

42. The method as defined by claim 40, wherein the measurements p are taken at a plurality of respectively separate measurement region shells.

43. The method as defined by claim 39, wherein said step (d) of generating a formation model includes generating a set of model amplitude components that define the transverse relaxation time distribution of the brine phase, and a further set of model amplitude components that define the transverse relaxation time distribution of the native oil, and a further set of model components that define the constituent viscosities of the native oil, and a model component that defines an oil base mud filtrate amplitude.

44. The method as defined by claim 43, wherein said step (d) of generating a formation model further includes generating a model component that represents the apparent ratio of brine longitudinal relaxation time to transverse relaxation time.

45. The method as defined by claim 36, further comprising the step of deriving, from the output model components, at least one porosity from the group consisting of water-filled porosity, oil-filled porosity, oil base mud filtrate-filled porosity, and total NMR-filled porosity of the formations.

46. The method as defined by claim 38, further comprising the step of deriving, from the output model components, the gas-filled porosity of the formations.

47. The method as defined by claim 36, further comprising the step of deriving, from the output model components, the free fluid porosity of the formations.

48. The method as defined by claim 36, further comprising the step of deriving, from the output model components, the bound fluid porosity of the formations.

49. The method as defined by claim 36, further comprising the step of deriving, from the output model components, at least one saturation from the group consisting of water saturation, oil saturation, and oil base mud filtrate saturation of the formations.

50. The method as defined by claim 38, further comprising the step of deriving, from the output model components, the gas saturation of the formations.

51. The method as defined by claim 43, further comprising the step of deriving, from the output model components, the viscosity of the native oil of the formations.

52. The method as defined by claim 43, further comprising the step of deriving, from the output model components, the diffusion constants of the native oil constituents of the formations.

53. The method as defined by claim 43, further comprising the step of deriving, from the output model components, the relaxation times of the native oil constituents of the formations.

54. The method as defined by claim 43, further comprising repeating said method for different separated regions of investigation in the formations, and further comprising the step of deriving, from the output model components for the different separated regions of investigation, a fluid saturation profile of the formations.

55. The method as defined by claim 39, wherein the measurements of steps (b) and (c) are taken while said logging device is moving through the borehole at a velocity v, and wherein said model signals are derived from the model based on computed magnetic resonance polarization functions which depend on wait time $W_p$ and the velocity v.

56. The method as defined by claim 55, wherein both longitudinal polarization functions and transverse relaxation times of the formation model are modified as a function of said velocity, v.

57. The method as defined by claim 39, wherein the magnetic field gradient in a measurement region of the formations includes a component for the applied gradient $G_p$ and a component for internal gradient in said measurement region of the formations resulting from magnetic susceptibility contrasts therein.

58. A method for determining properties of earth formations surrounding a borehole, comprising the steps of:
   (a) providing a logging device that is moveable through the borehole;
   (b) transmitting electromagnetic energy from said logging device into the formations, and receiving nuclear magnetic resonance spin echoes at said logging device;
   (c) performing step (b) a plurality of times, with a respective plurality of different transmitting and/or receiving conditions to obtain a plurality of measurements;
   (d) generating a formation model that includes a plurality of model components for a brine phase and also includes a plurality of native oil relaxation times for a native oil phase;
   (e) modifying the model components to optimize the model with respect to the measurement signals; and
   (f) outputting model components of the optimized model.

59. The method as defined by claim 58, wherein said step of generating a formation model comprises generating a model that further includes an oil base mud filtrate component.

60. The method as defined by claim 58, wherein said step of generating a formation model comprises generating a model that further includes a gas component.

61. The method as defined by claim 58, wherein said step of transmitting electromagnetic energy from said logging device and receiving nuclear magnetic resonance spin echoes at said logging device includes producing a static magnetic field in a region of investigation and generating sequences of magnetic field radio frequency pulses in the region of investigation and receiving sequences of nuclear magnetic resonance spin echoes, and wherein the applied static magnetic field gradient in the investigation region is $G_p$, and wherein the wait time between sequences is $W_p$, and the echo spacing is $TE_p$, and the number of received spin echoes of a sequence is $J_p$, and wherein said step (c) comprises performing step (b) a plurality of times with respective different values of at least one condition selected from the group consisting of $G_p$, $W_p$, $TE_p$, and $J_p$.

62. The method as defined by claim 61, wherein said step (c) comprises performing step (b) N times to obtain a suite of N measurements.

63. The method as defined by claim 62, wherein each of said measurements includes several repetitions of the pulse-echo sequences, and wherein said measurements comprise detection of spin echo amplitudes during the sequences.

64. The method as defined by claim 62, wherein the measurements p are taken at a plurality of respectively separate measurement region shells.

65. The method as defined by claim 64, wherein said shells are substantially cylindrical shells having radial extents of about 1 mm.

66. The method as defined by claim 58, further comprising the step of deriving, from the output model components, at least one porosity from the group consisting of water-filled porosity, oil-filled porosity and total NMR-filled porosity of the formations.

67. The method as defined by claim 59, further comprising the steps of deriving, from
the output model components, the oil base mud filtrate-filled porosity of the formations.

68. The method as defined by claim 60, further comprising the step of deriving, from the output model components, the gas-filled porosity of the formations.

69. The method as defined by claim 58, further comprising the step of deriving , from the output model components, the free fluid porosity of the formations.

70. The method as defined by claim 58, further comprising the step of deriving, from the output model components, the bound fluid porosity of the formations.

71. The method as defined by claim 58, further comprising the step of deriving, from the output model components, at least one saturation from the group consisting of water saturation and oil saturation of the formations.

72. The method as defined by claim 59, further comprising the step of deriving, from the output model components, the oil base mud filtrate saturation of the formations.

73. The method as defined by claim 60, further comprising the step of deriving, from the output model components, the gas saturation of the formations.

74. The method as defined by claim 61, further comprising repeating said method for different separated regions of investigation in the formations, and further comprising the step of deriving, from the output model components for the different separated regions of investigation, a fluid saturation profile of the formations.

75. The method as defined by claim 61, wherein the measurements of steps (b) and (c) are taken while said logging device is moving through the borehole at a velocity v, and wherein said model signals are derived from the model based on computed magnetic resonance polarization functions which depend on wait time W[] and the velocity v.

76. The method as defined by claim 61, wherein both longitudinal polarization functions and transverse relaxation times of the formation model are modified as a function of said velocity, v.

77. The method as defined by claim 61, wherein the magnetic field gradient in a measurement region of the formations includes a component for the applied gradient $G_p$ and a component for internal gradient in said measurement region of the formations resulting from magnetic susceptibility contrasts therein.

78. A method for determining properties of an earth formation core sample, comprising the steps of:
   (a) transmitting electromagnetic energy into the core sample, and receiving nuclear magnetic resonance spin echoes from the core sample;
   (b) performing step (a) a plurality of times, with a respective plurality of different transmitting and/or receiving conditions to obtain a plurality of measurements;
   (c) generating a formation model that includes a plurality of model components for a brine phase and a plurality of model components for a native oil phase;

(d) modifying the model components to optimize the model with respect to the measurement signals; and (e) outputting model components of the optimized model.

79. The method as defined by claim 78, wherein said step (d) of generating a formation model includes generating a set of model amplitude components that define the transverse relaxation time distribution of the brine phase, and a further set of model amplitude components that define the transverse relaxation time distribution of the native oil, and a further set of model components that define the constituent viscosities of the native oil.

80. A method for determining properties of an earth formation core sample, comprising the steps of:

(a) transmitting electromagnetic energy into the core sample, and receiving nuclear magnetic resonance spin echoes from the core sample;

(b) performing step (a) a plurality of times, with a respective plurality of different transmitting and/or receiving conditions to obtain a plurality of measurements;

(c) generating a formation model that includes model components for a brine phase, a native oil phase, and an oil base mud filtrate phase;

(d) modifying the model components to optimize the model with respect to the measurement signals; and (e) outputting model components of the optimized model.

81. A method for determining properties of an earth formation core sample, comprising the steps of:

(a) transmitting electromagnetic energy into the core sample, and receiving nuclear magnetic resonance spin echoes from the core sample;

(b) performing step (a) a plurality of times, with a respective plurality of different transmitting and/or receiving conditions to obtain a plurality of measurements;

(c) generating a formation model that includes a plurality of model components for a brine phase and also includes a plurality of native oil relaxation time for a native oil phase;

(d) modifying the model components to optimize the model with respect to the measurement signals; and (e) outputting model components of the optimized model.

82. The method as defined by claim 61 wherein step (c) further comprises the step of deriving a plurality of diffusion coefficients related to the native oil relaxation times.

* * * * *